(12) United States Patent
Ophardt et al.

(10) Patent No.: US 10,888,884 B2
(45) Date of Patent: Jan. 12, 2021

(54) DUAL PUMP HAND CLEANER FOAM DISPENSER

(71) Applicant: OP-Hygiene IP GmbH, Niederbipp (CH)

(72) Inventors: Heiner Ophardt, Arisdorf (CH); Andrew Jones, St. Anns (CA); Zhenchun Shi, Hamilton (CA)

(73) Assignee: OP-Hygiene IP GmbH, Niederbipp (CH)

( * ) Notice: Subject to any disclaimer, the term of this patent is extended or adjusted under 35 U.S.C. 154(b) by 0 days.

(21) Appl. No.: 16/448,395

(22) Filed: Jun. 21, 2019

(65) Prior Publication Data

US 2019/0314833 A1 Oct. 17, 2019

Related U.S. Application Data

(63) Continuation of application No. 15/493,692, filed on Apr. 21, 2017, now Pat. No. 10,421,085.

(51) Int. Cl.

| B05B 7/00 | (2006.01) |
|---|---|
| B05B 7/26 | (2006.01) |
| B05B 11/00 | (2006.01) |
| A47K 5/12 | (2006.01) |
| A61L 2/26 | (2006.01) |
| A61L 2/00 | (2006.01) |

(52) U.S. Cl.
CPC ............ *B05B 7/005* (2013.01); *A47K 5/1211* (2013.01); *A61L 2/26* (2013.01); *B05B 7/26* (2013.01); *B05B 11/0037* (2013.01); *B05B 11/0078* (2013.01); *B05B 11/3011* (2013.01); *B05B 11/3084* (2013.01); *B05B 11/3087* (2013.01); *B05B 11/3092* (2013.01); *A61L 2/0088* (2013.01); *A61L 2202/15* (2013.01)

(58) Field of Classification Search
CPC ......... B05B 7/005; B05B 7/0037; B05B 7/26; B05B 11/0037
USPC ......... 222/133, 135, 145.1, 145.5, 190, 255, 222/631
See application file for complete search history.

(56) References Cited

U.S. PATENT DOCUMENTS

| 3,557,004 | A | 1/1971 | Yolles |
|---|---|---|---|
| 3,760,986 | A | 9/1973 | Castner |
| 5,271,530 | A | 12/1993 | Uehira |
| 5,676,277 | A | 10/1997 | Ophardt |
| 7,303,099 | B2 | 12/2007 | Ophardt |
| 7,823,751 | B2 | 11/2010 | Ophardt |
| 8,272,539 | B2 | 9/2012 | Ophardt |
| 8,479,951 | B2 | 7/2013 | Ciavarella |
| 8,622,243 | B2 | 1/2014 | Ophardt |

(Continued)

*Primary Examiner* — Vishal Pancholi
(74) *Attorney, Agent, or Firm* — Thorpe North & Western, LLP

(57) ABSTRACT

A hand cleaner foam dispenser with a first pump arrangement that discharges a first liquid and first air from the atmosphere through a first foam inducing member into a mixing chamber and a second pump arrangement that discharges a second liquid into the mixing chamber, and in which there is a simultaneous discharge of the first liquid, first air and the second liquid from the mixing chamber through an outlet foam inducing member to produce a foamed product delivered onto a person's hand. Preferably, the second pump arrangement may discharge not only the second liquid, but also second air drawn from the atmosphere and discharge the second liquid and the second air through a second foam inducing member into the mixing chamber.

18 Claims, 15 Drawing Sheets

(56) References Cited

U.S. PATENT DOCUMENTS

| | | |
|---|---|---|
| 8,733,596 B2 | 5/2014 | Ophardt |
| 2005/0115988 A1 | 6/2005 | Law |
| 2005/0205600 A1 | 9/2005 | Ophardt |
| 2007/0278247 A1 | 12/2007 | Banks |
| 2008/0237261 A1 | 10/2008 | van der Heijden |
| 2013/0175296 A1 | 7/2013 | Gray |
| 2014/0197196 A1 | 7/2014 | Tederous |

DUAL PUMP HAND CLEANER FOAM DISPENSER

RELATED APPLICATION

This application is a continuation of co-pending U.S. patent application Ser. No. 15/493,692 filed Apr. 21, 2017 and claims the benefit of 35 U.S.C. 120.

SCOPE OF THE INVENTION

This invention relates to a method of dispensing multiple liquid streams to produce a mixed product preferably as a foam including air and more particularly to a hand cleaner dispenser utilizing two or more pump arrangements to dispense liquids mixed with air through foam inducing members as for discharge onto a person's hand as a resultant foamed product.

BACKGROUND OF THE INVENTION

Various hand cleaner foam dispensers are known with pump arrangements for simultaneously passing a liquid and air through a foam inducing member to produce a foamed product and discharge the foamed product onto a user's hand. Such foam dispensers for dispensing liquid from a single reservoir are well known and as for example are taught in U.S. Pat. No. 7,303,099 to Ophardt issued Dec. 4, 2007 and U.S. Pat. No. 8,272,539 to Ophardt et al. issued Sep. 25, 2012.

Hand cleaner foam dispensers are known in which a pump arrangement in which liquid from a single reservoir is mixed with air and discharged as foam onto a user's hand. The present inventor has appreciated that previously known devices do not provide hand cleaner foam dispensers in which two liquid streams, for example, from two different reservoirs may be mixed and delivered to a person's hand as a foam.

Proprietary hand cleaner compositions are known which are adapted when dispensed through a foam generating pump arrangement to produce a foamed product. Such cleaning compositions include alcohol and water compositions and liquid soap compositions. The present inventor has appreciated that with many known cleaning compositions, difficulties arise in creating foam with optimized characteristics for hand cleaning. Difficultly in producing advantageous foam for hand cleaning particularly arises in respect of cleaning compositions including alcohol. Cleaning compositions containing alcohol have enhanced cleaning as the amount of alcohol is increased, for example, to above 40% by volume alcohol or more preferably above 60% by volume alcohol to provide for enhanced cleaning, however, difficulties in producing advantageous foam for hand cleaning compositions containing alcohol increases as the concentration of alcohol is increased, particularly when the concentration of alcohol is increased above 40% by volume or above 60% volume.

Proprietary hand cleaning compositions may require particular additives such as foaming agents, surfactants and foam stabilizers. The present inventor has appreciated that difficulties arise in developing cleaning composition with suitable components to provide an advantageous foam for cleaning since legal protection on proprietary cleaning compositions can restrict the use of particular compositions.

The present inventor has also appreciated that known pump arrangements to produce foam that draw liquid from a single reservoir and/or having a single pump arrangement limit the extent to which advantageous foam may be developed and/or different cleaning compositions and additives may be utilized.

SUMMARY OF THE INVENTION

To at least partially overcome these disadvantages of previously known devices, the present invention provides a hand cleaner foam dispenser with a first pump arrangement that discharges a first liquid and first air from the atmosphere through a first foam inducing member into a mixing chamber and a second pump arrangement that discharges a second liquid into the mixing chamber, and in which there is a simultaneous discharge of the first liquid, first air and the second liquid from the mixing chamber through an outlet foam inducing member to produce a foamed product delivered onto a person's hand. Preferably, the second pump arrangement may discharge not only the second liquid, but also second air drawn from the atmosphere and discharge the second liquid and the second air through a second foam inducing member into the mixing chamber.

To overcome the disadvantages of previously known devices the present invention also provides a method of creating foam, preferably in a hand clean foam dispenser, comprising discharging a first liquid and a first air simultaneously through a first foam inducing member into a mixing chamber; discharging a second liquid into the mixing chamber; and simultaneously discharging the first liquid, first air and second liquid from the mixing chamber through an outlet foam inducing member. Preferably, the method includes discharging the second liquid and second air from the atmosphere simultaneously through the second foam inducing member into the mixing chamber and, subsequently, simultaneously discharging the first liquid, first air, second liquid and the second air from the mixing chamber through the foam inducing member.

In one aspect, the present invention provides a hand cleaner foam dispenser comprising: a first reservoir containing a first fluid; a first pump arrangement operative to draw the first fluid from the first reservoir and to draw first air from the atmosphere and to simultaneously discharge the first fluid and the first air through a first foam inducing member into a mixing chamber; a second reservoir containing a second fluid; a second pump arrangement operative to draw the second fluid from the second reservoir and to discharge the second fluid into the mixing chamber; the mixing chamber open to a discharge outlet via an outlet passageway; an outlet foam inducing member across the outlet passageway, the first pump arrangement and the second pump arrangement operative to simultaneously discharge the first fluid and first air through the first foam inducing member into the mixing chamber and the second fluid into the mixing chamber, forcing the flow of the first fluid, the first air, and the second fluid simultaneously from the mixing chamber through the outlet foam inducing member and out the discharge outlet onto a person's hand. Preferably, the second pump arrangement is operative to draw the second fluid from the second reservoir and to draw second air from the atmosphere and to simultaneously discharge the second fluid and the second air through a second foam inducing member into the mixing chamber, through a second foam inducing member; the first pump arrangement and the second pump arrangement operative to simultaneously discharge the first fluid and first air through the first foam inducing member into the mixing chamber and the second fluid and the second air through the second foam inducing member into the mixing chamber, forcing the flow of the first fluid, the first air, the second fluid and the second air simultaneously from the mixing chamber through the outlet foam inducing member and out the discharge outlet onto a person's hand.

In another aspect, the present invention provides a method of operation of a hand cleaner foam dispenser, the hand cleaner foam dispenser comprising:
a first reservoir containing a first fluid;
a first pump arrangement operative to draw the first fluid from the first reservoir and to draw first air from the atmosphere and to simultaneously discharge the first fluid and the first air through a first foam inducing member into a mixing chamber;
a second reservoir containing a second fluid;
a second pump arrangement operative to draw the second fluid from the second reservoir and to discharge the second fluid into the mixing chamber;
the mixing chamber open to a discharge outlet via an outlet passageway;
an outlet foam inducing member across the outlet passageway,
the method comprising operating the first pump arrangement and the second pump arrangement to simultaneously discharge into the mixing chamber both (a) the first fluid and first air through the first foam inducing member and (b) the second fluid into the mixing chamber, thereby forcing the flow simultaneously from the mixing chamber through the outlet foam inducing member and out the discharge outlet onto a person's hand of the first fluid, the first air, and the second fluid. Preferably, the second pump arrangement is operative to draw the second fluid from the second reservoir and to draw second air from the atmosphere and to simultaneously discharge the second fluid and the second air through a second foam inducing member into the mixing chamber; and the method comprises operating the first pump arrangement and the second pump arrangement to simultaneously discharge into the mixing chamber both (a) the first fluid and first air through the first foam inducing member and (b) the second fluid and the second air through the second foam inducing member into the mixing chamber, thereby forcing the flow simultaneously from the mixing chamber through the outlet foam inducing member and out the discharge outlet onto a person's hand of the first fluid, the first air, the second fluid and the second air.

DETAILED DESCRIPTION OF THE DRAWINGS

Further aspects and advantages will occur from the following description taking together with the accompanying drawings in which.

Figure 11:
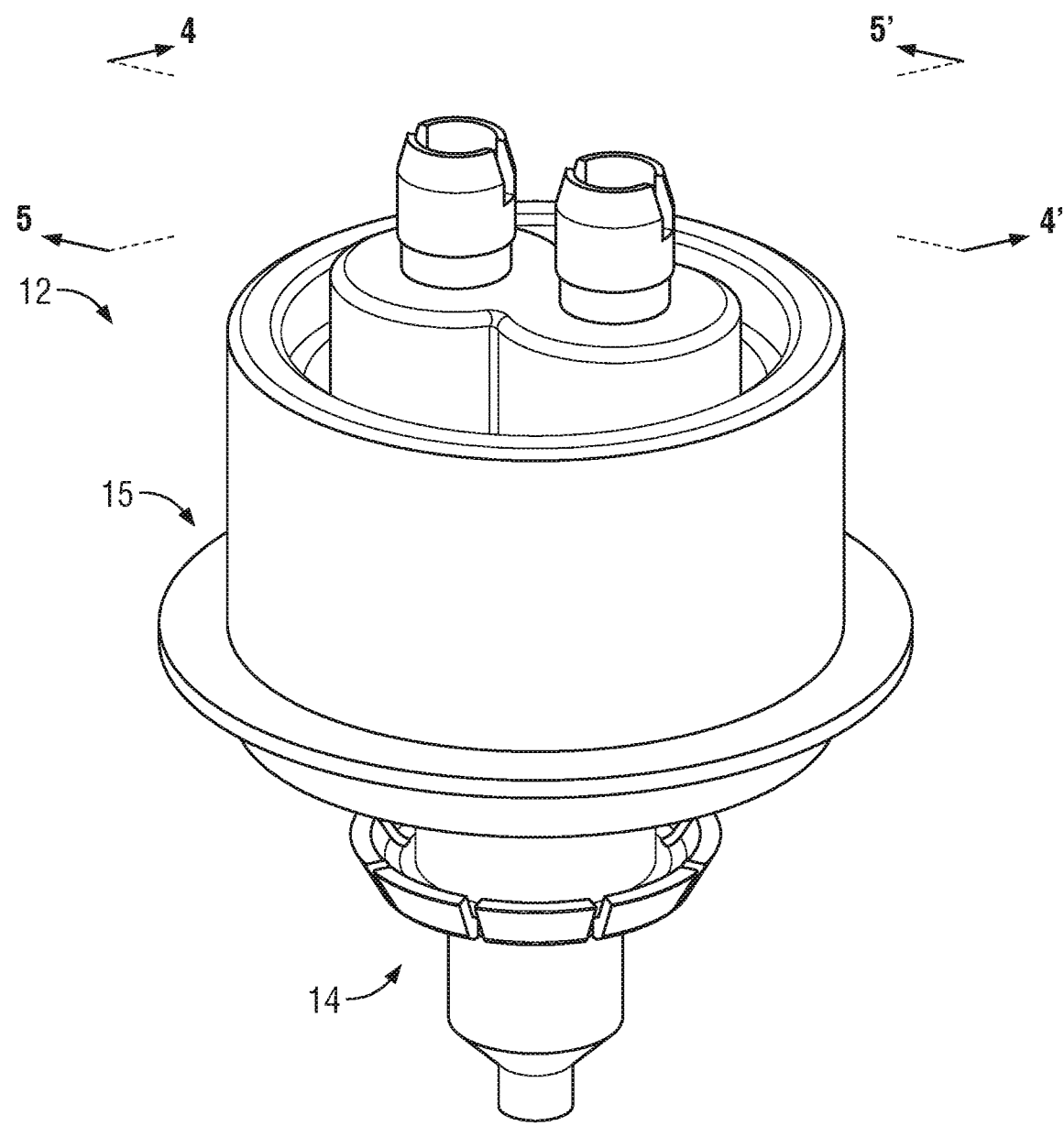
FIG. 11 is a pictorial view of a fourth embodiment of a pump assembly in accordance with the present invention showing the piston-forming element in a retracted condition relative to the piston chamber-forming body.
Figure 14:
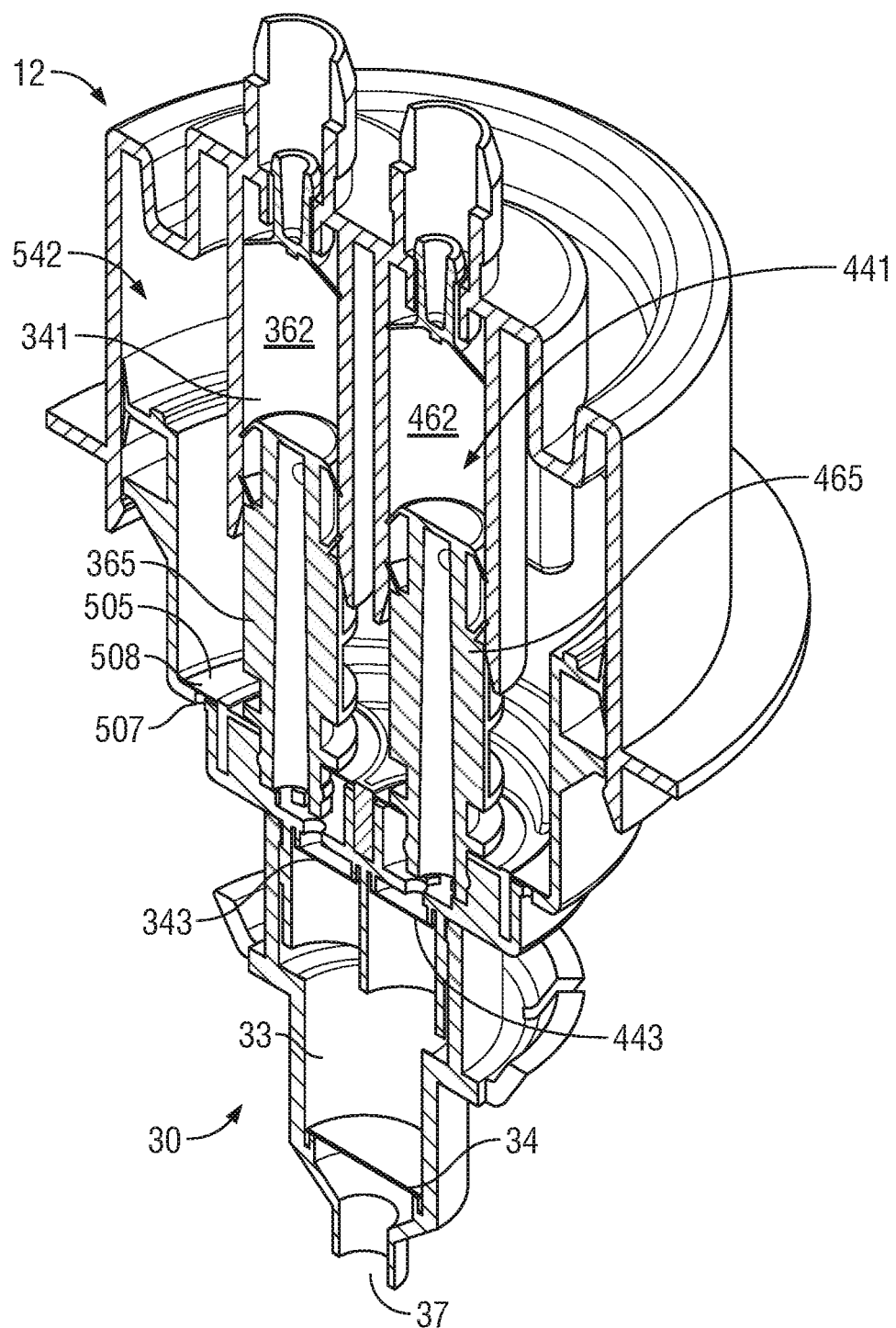
Figure 15:
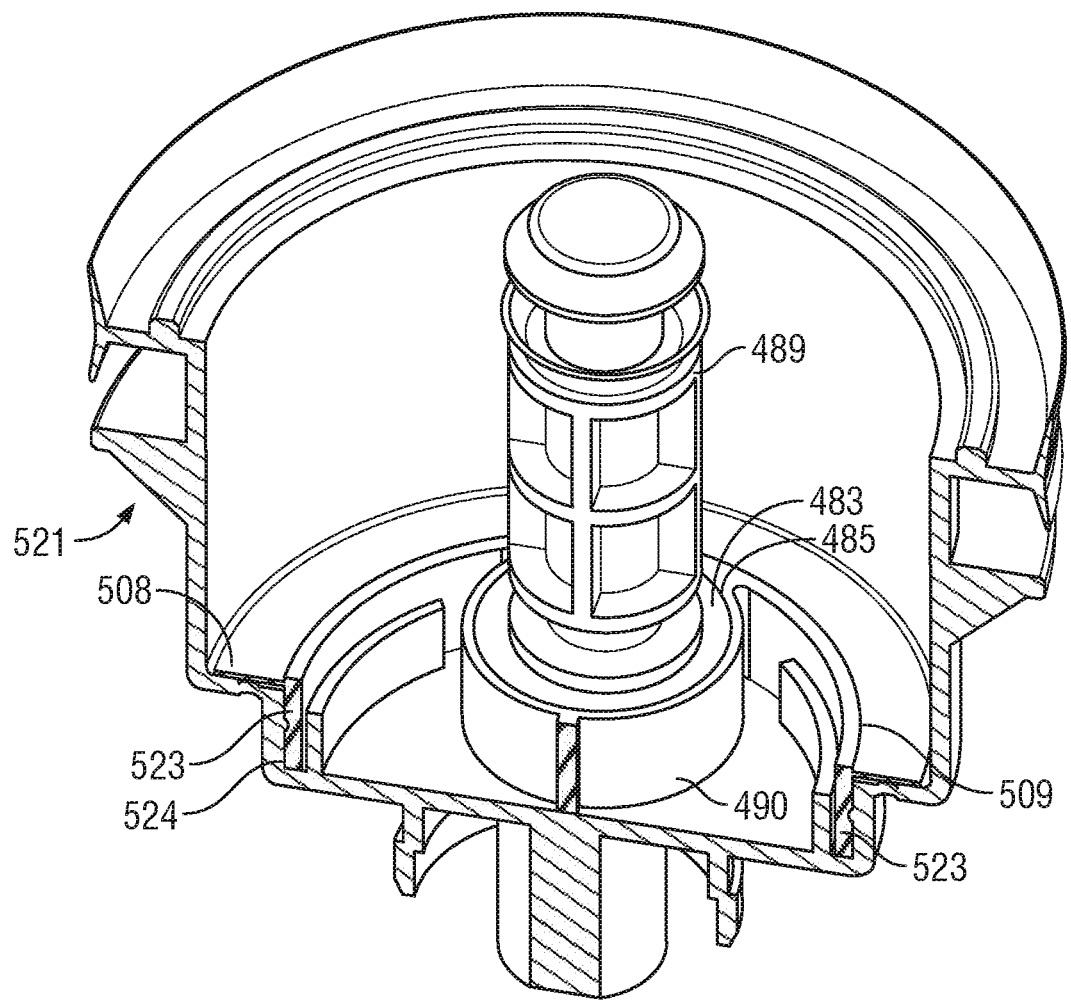

FIG. 14 is a pictorial cross-sectional front view of the pump assembly of FIG. 11 along section 4-4 in FIG. 11 but showing the piston-forming member in an extended condition relative to the piston chamber-forming body; and FIG. 15 is a pictorial cross-sectional side view of the piston-forming element of the pump assembly of FIG. 11 along section 5-5' in FIG. 11 normal to section line 4-4'.

DETAILED DESCRIPTION OF THE DRAWINGS

Figure 1:
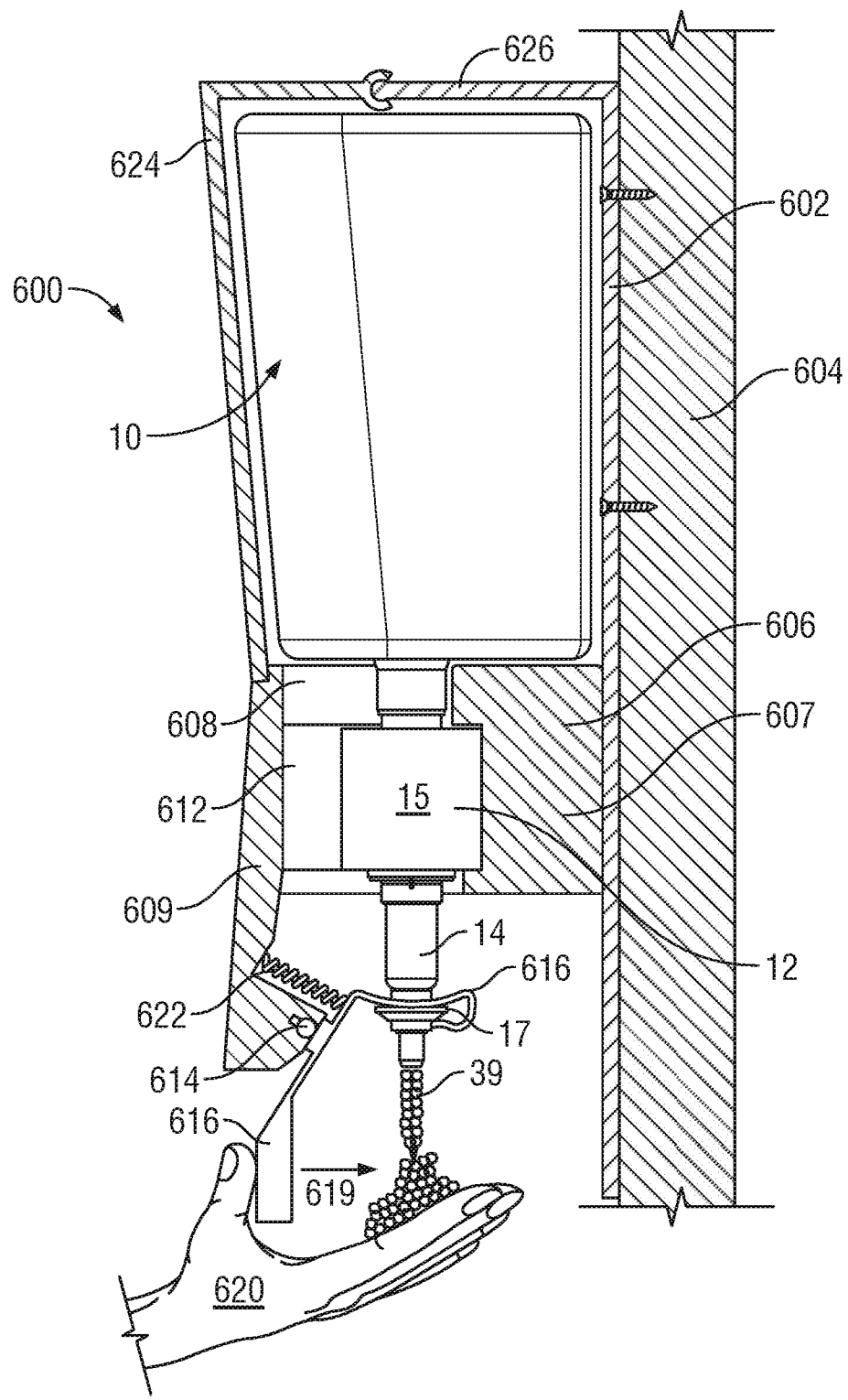
FIG. 1 is a partially cutaway schematic side view of a first embodiment of a hand cleaner dispenser including a removable and replaceable cartridge comprising a reservoir assembly and a pump assembly in accordance with the present invention.

Reference is made to FIG. 1 which schematically shows in side view a manually operated hand cleaner foam dispenser 600 in accordance with the present invention. The dispenser 600 is adapted to removably receive a cartridge 10. In FIG. 1, the dispenser 600 is shown in side cross-section other than an activating lever 610 which is schematically shown in side view and not cross-sectioned. In FIG. 1, a user's hand 620 and the cartridge 10 are also shown in side view and not cross-sectioned.

In FIG. 1, the dispenser 600 includes a back plate 602 as for mounting of the dispenser 600 to a building wall 604. A support plate 606 extends forwardly from the back plate 604 to support and receive the cartridge 10. The support plate 606 has a rear portion 607, two side arms 608 (only one of which is seen) and a forward portion 609. The side arms 608 extend forwardly from the rear portion 607 to support the forward portion 609 forming a lower front wall of the dispenser 600. The support plate 606 has an opening 612 extending downwardly therethrough defined between the side arms 608 and between the forward portion 609 and the rear portion 607 via which opening 612 the cartridge 10 may be inserted downwardly and then slid rearwardly for secure engagement of a piston chamber-forming body 15 of a pump assembly 12 of the cartridge 10 on the support plate 606. The activating lever 610 is journalled to the forward portion 609 for pivoting about a horizontal axis 614. An upper end of the lever 610 carries a hook 616 to engage an engagement flange 17 on a piston-forming member 14 of the pump assembly 12 and couple the lever 610 to the piston-forming member 14 such that by movement of a lower handle end of the lever 610 in the direction indicated by the arrow 619 manually by the hand 620 of a user slides the piston-forming member 14 relative the body 15 upwardly and inwardly in a retraction stroke to the retracted position shown in FIG. 1 thereby dispensing a final foamed product 39 downwardly onto the user's hand 620. On release of the lower handle end of the lever 610, a spring 622 biases the upper end of the lever 610 downwardly so that the lever 610 moves the piston-forming element 14 relative the body 15 outwardly in an extension stroke to an extended position not shown in FIG. 1. A cover member 624 is hinged at 625 to an upper forward extension 626 of the back plate 604 so as to permit manual removal and replacement of the cartridge 10.

Figure 2:
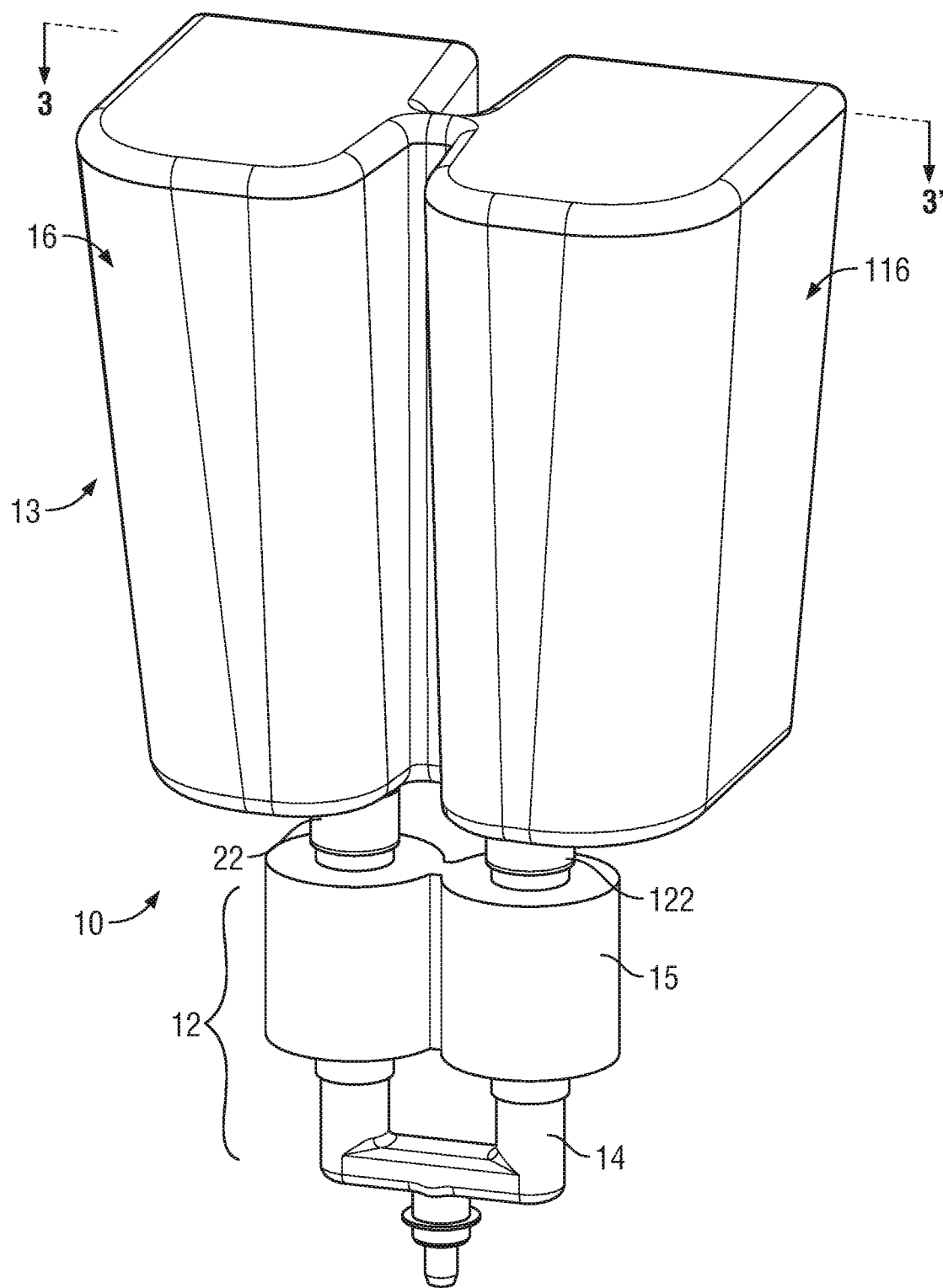
FIG. 2 is a pictorial view of the cartridge shown in FIG. 1.

Reference is made to FIG. 2 which shows a pictorial front view of the cartridge 10 which comprises the pump assembly 12 and a reservoir assembly 13. The pump assembly 12 comprises the piston-forming member 14 and the piston chamber-forming body 15.

Figure 3:
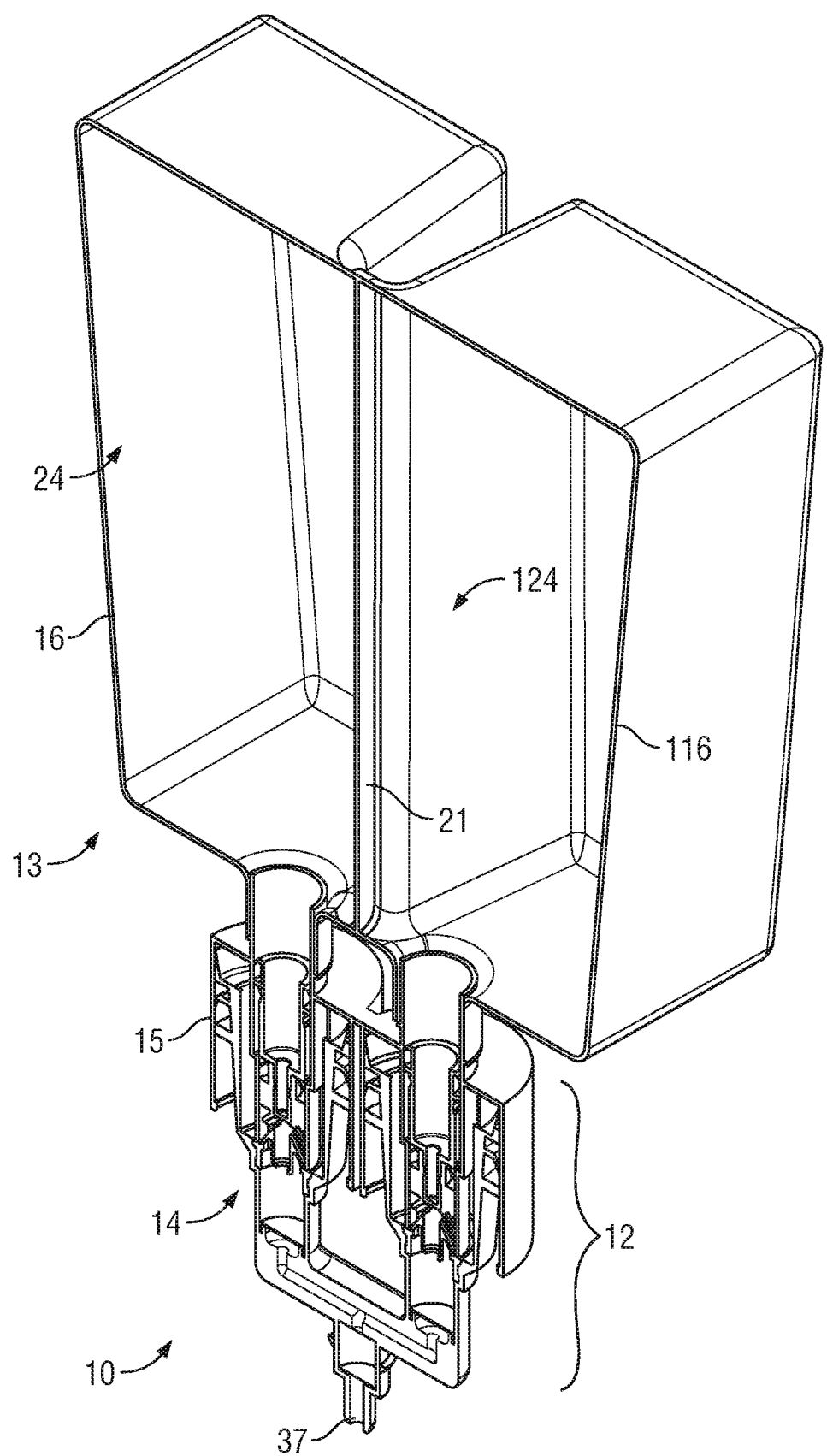
FIG. 3 is a cross-sectional pictorial front view of the cartridge of FIG. 2 in a vertical cross-section side-to-side along section line 3-3' in FIG. 2 centrally through the pump assembly.
Figure 4:
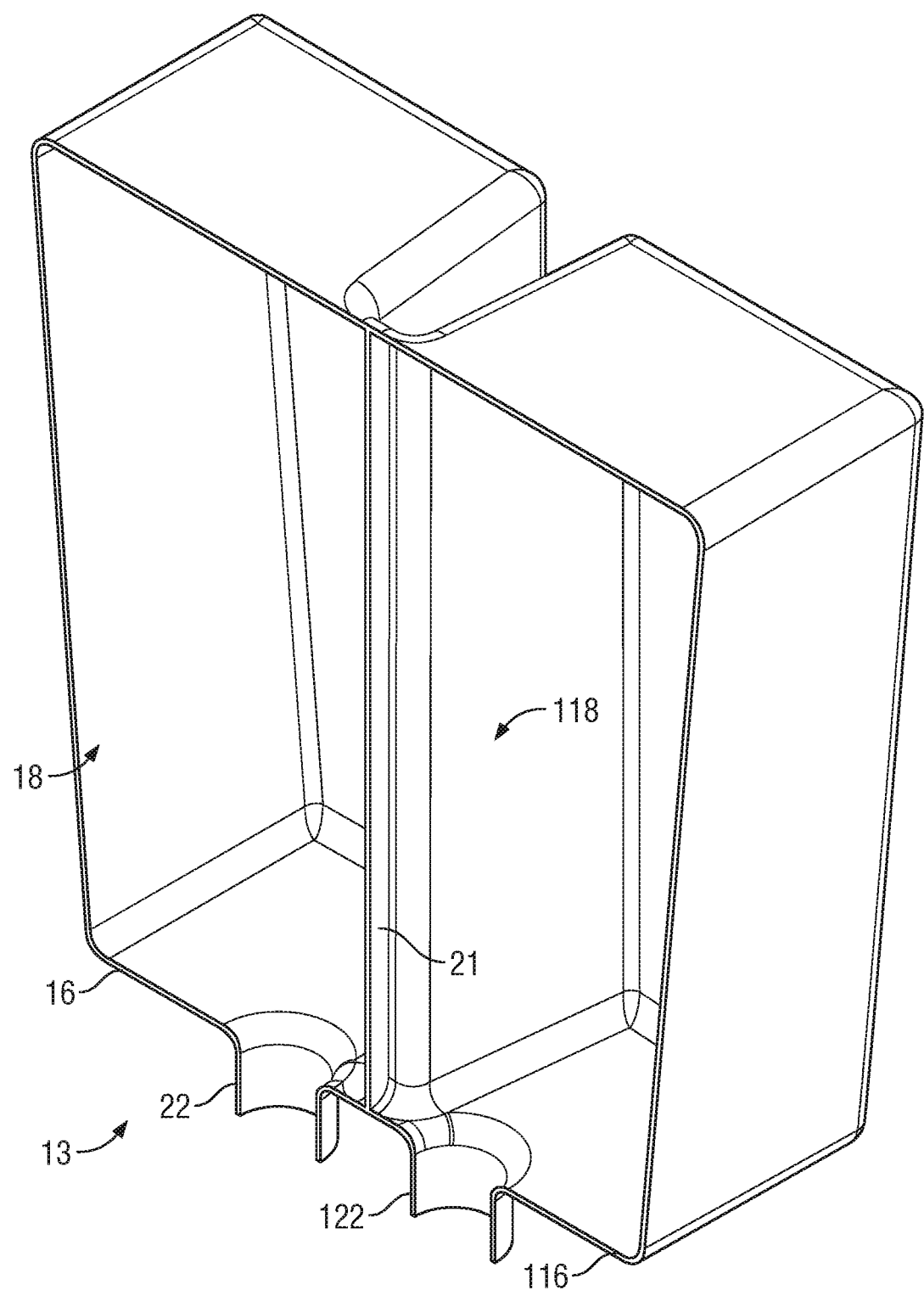
FIG. 4 is an enlarged cross-sectional pictorial front view the same as FIG. 3, but merely showing the reservoir assembly.

Reference is made to FIGS. 3 and 4, showing the reservoir assembly 13 as comprising a first reservoir 16 and second reservoir 116. The first reservoir 16 has an enclosed first reservoir chamber 18 and the second reservoir 116 has an enclosed second reservoir chamber 118. The first reservoir chamber 18 and the second reservoir chamber 118 are separated from each other by reason of an intermediate wall 21. The first reservoir 16 has a cylindrical first outlet neck 22 and the second reservoir 116 has a cylindrical second outlet neck 122.

The first reservoir 16 contains a first liquid 24 and the second reservoir 116 contains a second liquid 124.

Figure 6:
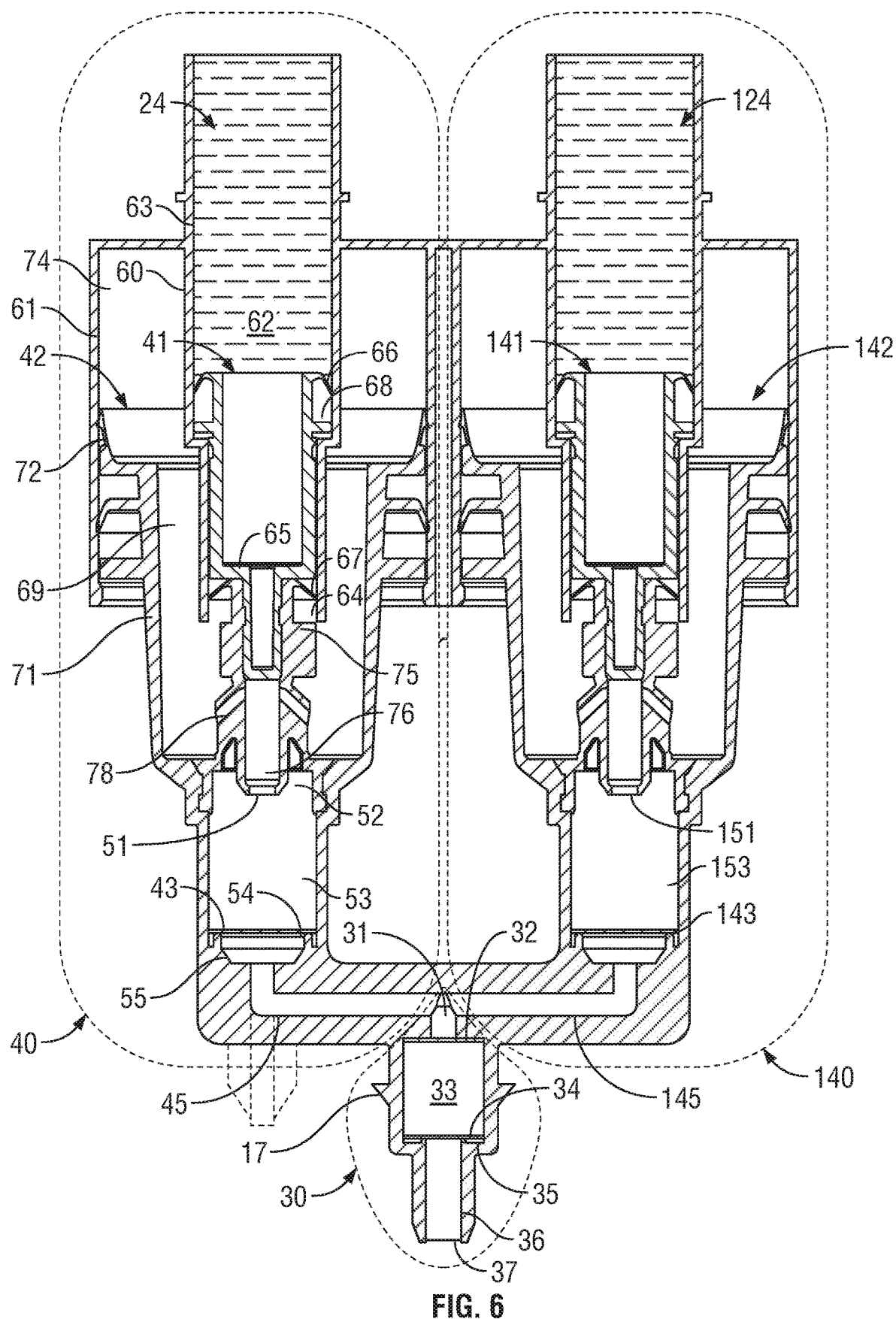
FIG. 6 is a cross-sectional front view of the pump assembly of FIG. 3 but with the piston-forming member in an extended position relative to the piston chamber-forming body.
Figure 7:
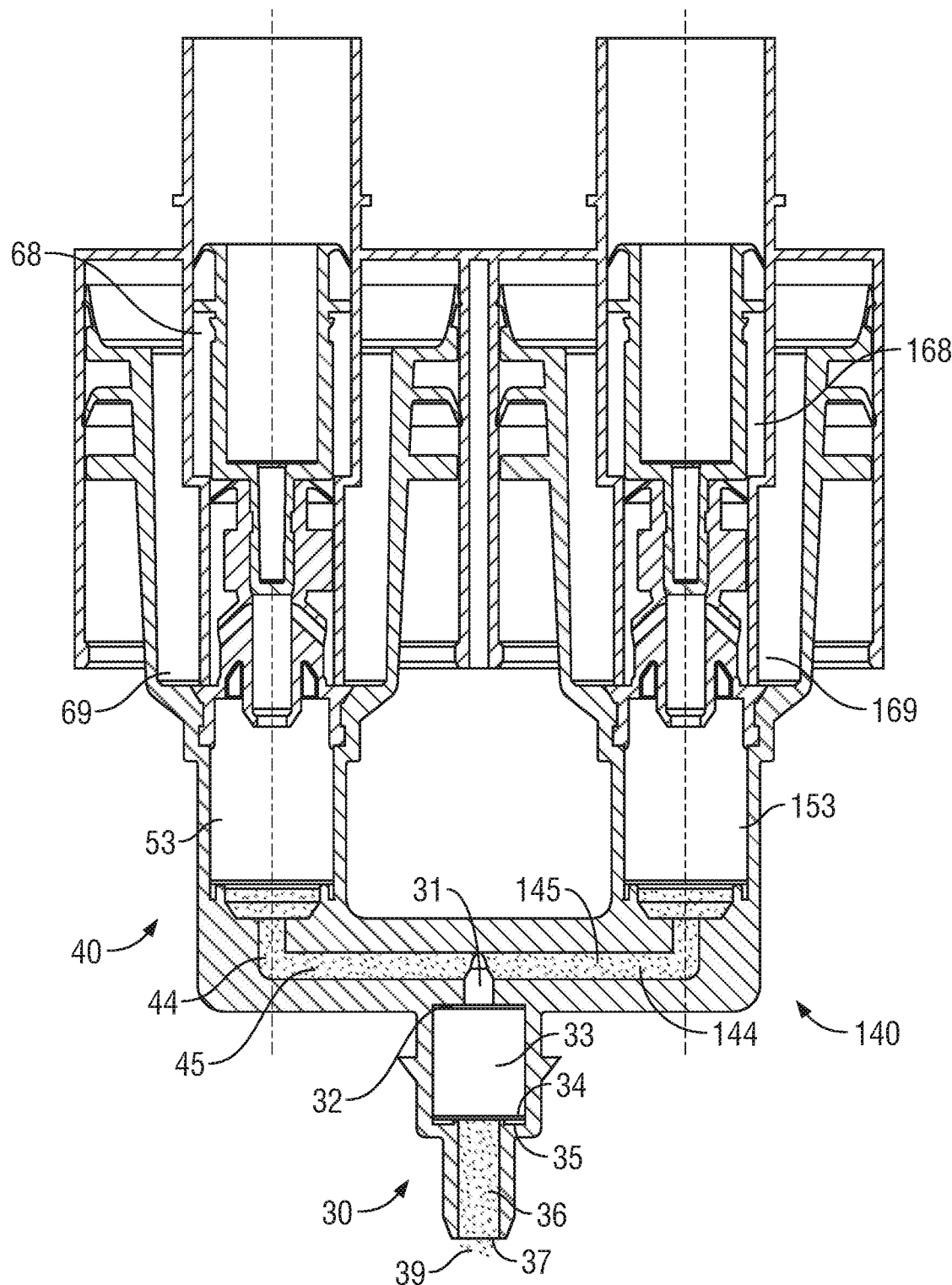
FIG. 7 is a cross-sectional front view the same as FIG. 6 but showing the piston-forming member in a retracted condition relative to the piston chamber-forming body.

The pump assembly 12 is described with reference to FIGS. 2, 3, 5, 6 and 7. As can be seen in the exploded view of FIG. 5, the pump assembly 12 comprises the piston-forming member 14 and the piston chamber-forming body 15. The piston-forming member 14 is reciprocally slidable relative to the piston chamber-forming body 15 for reciprocal movement in a cycle of operation between an extended position as shown in FIG. 6 and a retracted position as shown in FIG. 7 as well as in each of FIGS. 1, 2 and 3. The cycle of operation comprises a retraction stroke in moving from the extended position to the retracted position and an extension stroke in moving from the retracted position to the extended position.

Reference is made to FIG. 6 which shows that the pump assembly 12 comprising the piston-forming member 14 and the piston chamber-forming body 15 provide as schematically identified within the encircling dashed lines:

a foaming discharge arrangement 30;
a first foaming pump arrangement 40; and
a second foaming pump assembly 140.

The foaming discharge arrangement 30 comprises a mixing chamber 33 with a mixing inlet passageway 31 leading to an inner end 32 of the mixing chamber 33 and a discharge passageway 36 leading from an outer end 35 of the mixing chamber 33 to a discharge outlet 37. Proximate the outer end 35 of the mixing chamber 33 there is provided an outlet foam inducing member 34 comprising a screen with a plurality of small openings through the screen.

The first foaming pump arrangement 40 has a configuration functionally equivalent to that disclosed in FIGS. 2 to 4 of U.S. Pat. No. 8,272,539 to Ophardt issued Sep. 25, 2012, the disclosure of which is incorporated herein by reference. The second foaming pump assembly 140 is identical to the first foaming pump assembly 40.

The first foaming pump arrangement 40 comprises a first liquid pump 41 and a first air pump 42 which cooperate in a cycle of operation of reciprocal movement of the piston-forming element 14 and the piston chamber-forming body 15:

(a) to draw in first air from the atmosphere;
(b) to draw the first liquid 24 from the first reservoir 16; and
(c) to simultaneously discharge the first liquid 24 and the first air through a first foam inducing member 43, forming a first intermediate product 44 shown on FIG. 7 that passes into a first discharge passageway 45 and into the mixing inlet passageway 31.

In particular in a retraction stroke in movement of the piston-forming element 14 relative the piston-chamber forming body 15 from the extended position of FIG. 6 to the retracted position of FIG. 7, the first foaming pump arrangement 40 simultaneously discharges the first liquid 24 and first air through the first foam inducing member 43 and via the first discharge passageway 45 into the mixing inlet passageway 31.

The second foaming pump arrangement 140 comprises a second liquid pump 141 and a second air pump 142 which cooperate in a cycle of operation of reciprocal movement of the piston forming element 14 and the piston chamber forming body 15:

(a) to draw in second air from the atmosphere;
(b) to draw the second liquid 124 from the second reservoir 116; and
(c) to simultaneously discharge the second liquid 124 and the second air through a second foam inducing member 143, forming a second intermediate product 144 as shown on FIG. 7 that passes into a second discharge passageway 145 and into the mixing inlet passageway 31.

In particular in a retraction stroke in movement of the piston-forming element 14 relative the piston chamber-forming body 15 from the extended position of FIG. 6 to the retracted position of FIG. 7, the second foaming pump arrangement 140 simultaneously discharges the second liquid 124 and the second air through the second foam inducing member 143 and via the second discharge passageway 145 into the mixing inlet passageway 31.

As a result of the simultaneous operation of the first foaming pump arrangement 40 and the second foaming pump arrangement 140 in a retraction stroke, the first liquid 24 and first air (as the first intermediate product 44) and the second liquid 25 and the second air (as the second intermediate product 144) are simultaneously passed into the outlet mixing chamber 33 and forced through the outlet foam inducing member 34 to be discharged out the discharge outlet 37 as a final product 39.

The first foaming pump arrangement 40 includes a first discharge outlet 51 through which the first liquid 24 and the first air are directed into an inner end 52 of a first mixing chamber 53. At an outer end 54, the first mixing chamber 53 carries the first foam inducing member 43 as a screen. The first liquid 24 and the first air are passed through the foam inducing member 43 into a funnelling entrance 55 to the first discharge passageway 45. The first discharge outlet 51 has a reduced cross-sectional area compared to the cross-sectional area of the first mixing chamber 53 as is believed advantageous towards mixing of the first liquid 24 and the first air prior to passing through the first foam inducing member 43. In the embodiment of FIG. 6, the second foaming pump arrangement 140 similarly has similar second discharge outlet 151 and a second mixing chamber 153. As seen in FIG. 6, each of the outlet mixing chamber 33, the first mixing chamber 53 and the second mixing chamber 153 are similar in their physical configuration. However, providing each mixing chamber to have an enlarged cross-sectional area compared to the outlet or passageway leading into that mixing chamber is not necessary and a mixing chamber may be considered to be formed at any place where the respective discharged liquids and/or air are mixed.

The first liquid pump 41 comprises a stepped first liquid chamber 62 including a larger diameter inner liquid chamber 63 and a smaller diameter outer liquid chamber 64. A first liquid piston 65 is coaxially slidable within the first liquid chamber 62. The first liquid piston 65 notably has an inner disc 66 engaged within the inner liquid chamber 63 and permitting only one-way flow of liquid outwardly. The first liquid piston 65 has an outer disc 67 engaged with the outer liquid chamber 64 and permitting only one-way liquid flow outwardly. A first liquid compartment 68 is defined radially between the first liquid chamber 62 and the first liquid piston 65 and axially between the inner liquid disc 66 and the outer liquid disc 67. With the axial movement of the first liquid piston 65 relative to the first liquid chamber 62, the volume of the first liquid compartment 68 changes. The volume of the first liquid compartment 68 increases in a retraction stroke and decreases in an extension stroke.

An outer end of the outer liquid chamber 64 opens into an air compartment 69 of the first air pump 42. In a retraction stroke, the first liquid pump 41 draws the first liquid 24 into the first liquid compartment 68. In a withdrawal stroke, the first liquid pump 41 discharges the first liquid 24 from the first liquid compartment 68 into a lower portion of the air compartment 69.

The first air pump 42 is coaxially disposed annularly about the first liquid pump 41. The air pump 42 has a first air piston 71 carrying an inner disc 72 at an inner end therein which sealably engages with an outer air chamber wall 61 of an air chamber 74 formed annularly about first the liquid chamber 62. The first air piston 61 includes a hollow center stem 75 with a central passageway 76 coaxially there through leading to the first discharge outlet 51. The first air compartment 69 is defined between the first air piston 71 and the air chamber 74 which varies in volume with coaxial sliding of the first air piston 71. Angled passageways 78 are provided from a lower portion of the first air compartment 69 into the central passageway 76 of the stem 75. In a retraction stroke, the first air within the first air compartment 69 and the first liquid 24 within the first air compartment 69 are discharged via the angled passageways 78, the central passageway 76 through the first discharge outlet 51 and hence into the first mixing chamber 33. In a retraction stroke, the volume of the first air compartment 69 increases and draws atmospheric air into the first air compartment 69 from the discharge outlet 37 through the foam discharge arrangement 30 and inwardly through the first discharge passageway 45, through the first foam inducing member 43, through the first mixing chamber 53, the first discharge outlet 51 the central passageway 76 and the angled passageways 78 into the first air compartment 69.

Figure 5:
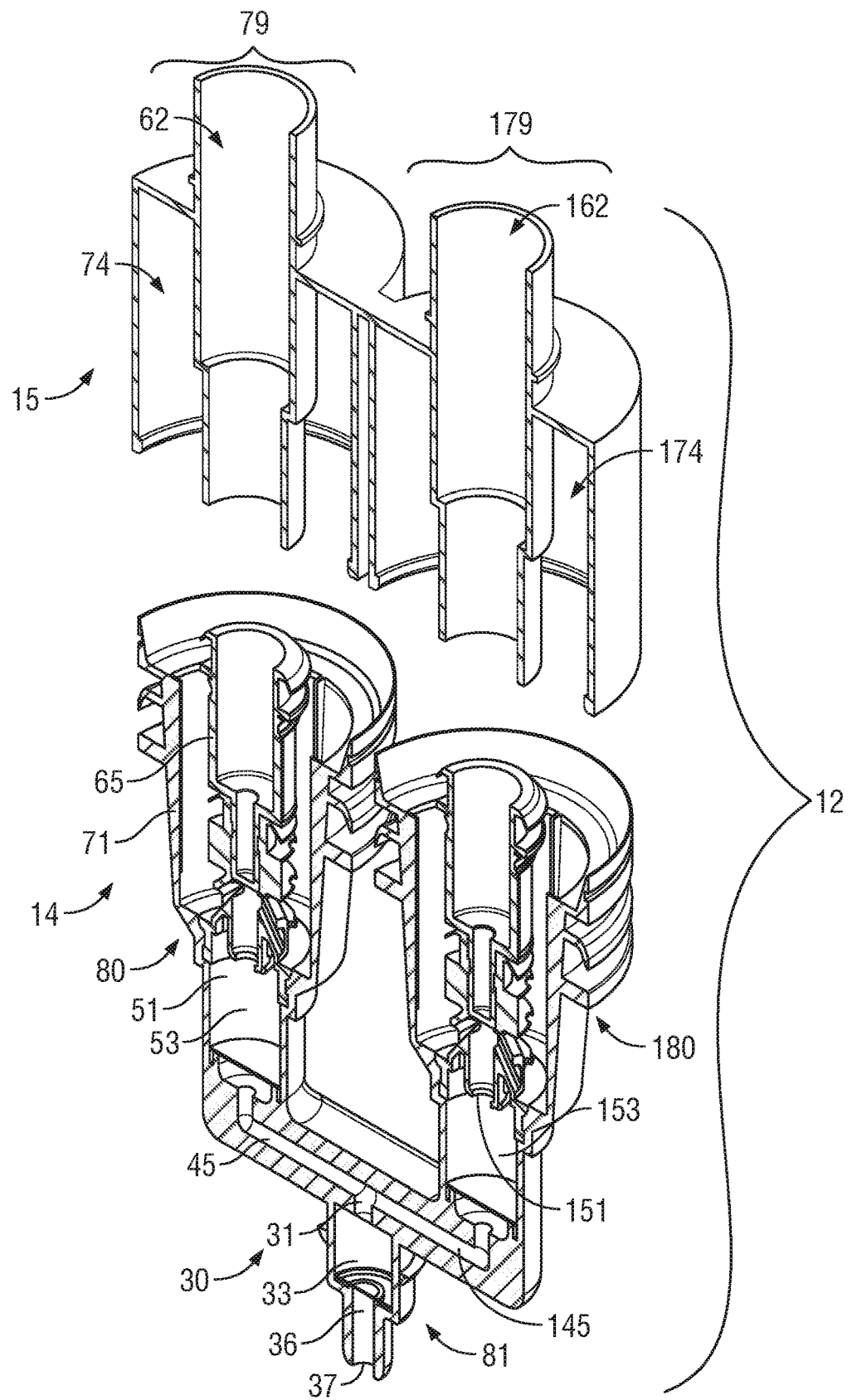
FIG. 5 is an exploded cross-section pictorial front view the same as FIG. 3 but merely showing a piston-forming member and a piston chamber-forming body of the pump assembly.

As best seen in FIG. 5, the first liquid chamber 62 and the first air chamber 74 are formed as a unitary member indicated as the first chamber body 79. The first liquid piston 65 and the first air piston 71 are also fixably coupled together forming a first piston member 80 including the first mixing chamber 53 and the first discharge passageway 45. As seen in FIG. 6, with the first foaming pump arrangement 40 identical to the second foaming pump arrangement 140, the second foaming pump arrangement 140 similarly comprises a second liquid pump 141 and a second air pump 142. A second chamber body 179 is integrally formed as a unitary member with the first chamber body 79. As seen in FIG. 5, the first piston element 80 and a second piston element 180 are mechanically coupled to the foaming discharge arrangement 30. Each of the first piston element 80 and the second piston element 180 have their respective first discharge passageway 45 and second discharge passageway 145 discharge into the inlet passageway 31 to the outlet mixing chamber 33. The foaming discharge arrangement 30 provides in effect a discharge manifold 81 for discharge from the first piston element 80 and the second piston element 180 into the outlet mixing chamber 33. This notional discharge manifold carries the first discharge passageway 45, the second discharge passageway 145, the inlet passageway 31, the outlet mixing chamber 33, and the discharge passageway 36.

The first foaming pump arrangement 40 comprises the first liquid pump 41 and the first air pump 42 utilizing in the embodiment of FIG. 6 as the first liquid pump 41 a stepped chamber displacement piston pump. In the first liquid pump 41, the volume of the first liquid 24 discharged in a stroke of operation is determined as the difference in cross-sectional area between the larger inner liquid chamber 63 and the smaller outer liquid chamber 64 multiplied by the length of the stroke. In the first air pump 42, the volume of the first air (at atmospheric pressure) discharged in a stroke of operation is determined as the cross-sectional area of the annular space between an outer air chamber wall 61 and an inner air chamber wall 60 multiplied by the length of the stroke of operation.

Preferably, in accordance with the present invention the first fluid 24 is a liquid which when discharge with the first air through the first foam inducing member 43 produces the first intermediate product 44 as a first foam. Preferably, the second fluid is a liquid which when discharged through with the second air through the second foam inducing member 143 produces the second intermediate product 145 as a second foam. However, in accordance with the present invention the first fluid 24 may be a liquid which when discharged with the first air through the first foam inducing member 43 produces the first intermediate product as a first foam and the second fluid 124 is a liquid which when discharged with the second air through the second foam inducing member 143 provides the second intermediate product 144 as a mixture of liquid and air which is not a foam, is a foam having poor foam characteristics for cleaning, or is a partial foam.

As one example, first fluid 124 comprises a first alcohol and water solution including a first foaming agent and not greater than 40% by volume alcohol and the second fluid 124 comprises a second alcohol and water solution with sufficiently greater than 40% volume by alcohol such that in the final product 39 discharged the volume ratio of alcohol to water is greater than 50%, more preferably 60%, more preferably 70% and, more preferably, 80%. In this example, preferably in the first liquid 24 the first foaming agent is provided in the first fluid 124 as comprising a base amount plus an additional excess amount. The base amount is the amount of the first foaming agent required to foam the first liquid 24 that passes through the first foam inducing member 43. The excess amount of the first foaming agent is preferably selected to be sufficient to foam the second fluid 124 as discharged in the cycle of operation if the second fluid 124 included the excess amount with the first foaming agent when the second fluid 24 is passed through the second foam inducing member 143.

Additionally, the first foaming agent 24 optionally includes a first foam stabilizing agent provided in the first fluid 24 to comprise a base amount plus an additional excess amount. The base amount is an amount of the first foam stabilizing agent required to stabilize the first intermediate product 43. The excess amount of the first foam stabilizing agent is at least sufficient to stabilize a second intermediate foam product that would be produced from the second liquid 124 if the second liquid 124 included the excess amount of the first foam stabilizing agent and the second fluid 124 is passed through the second foam inducing member 143 together with the excess amount.

Second Embodiment

Figure 8:
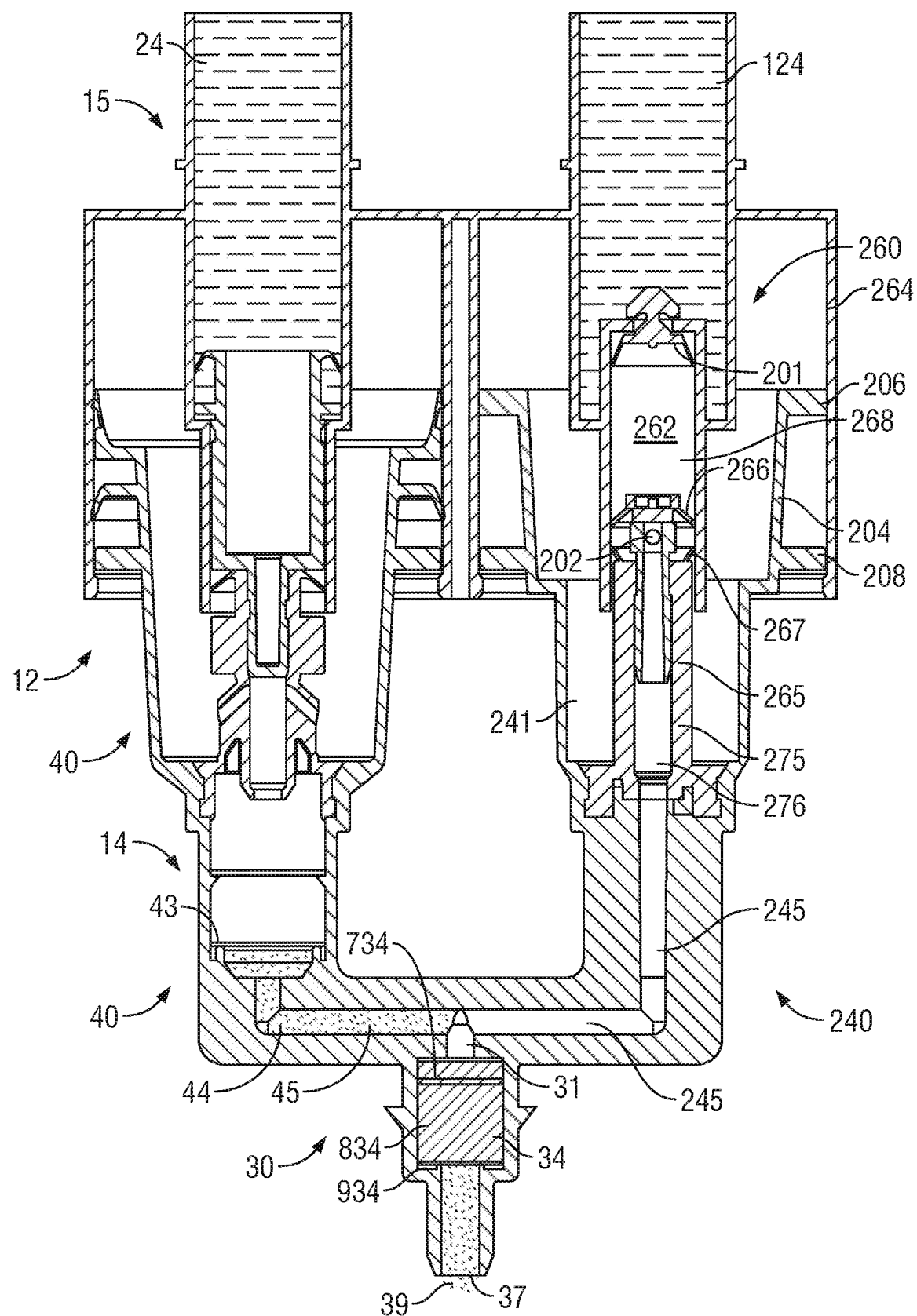
FIG. 8 is a cross-sectional front view of a second embodiment of a pump assembly in accordance with the present invention showing the piston-forming member in an extended condition relative the piston chamber-forming body similar to FIG. 6.
Figure 9:
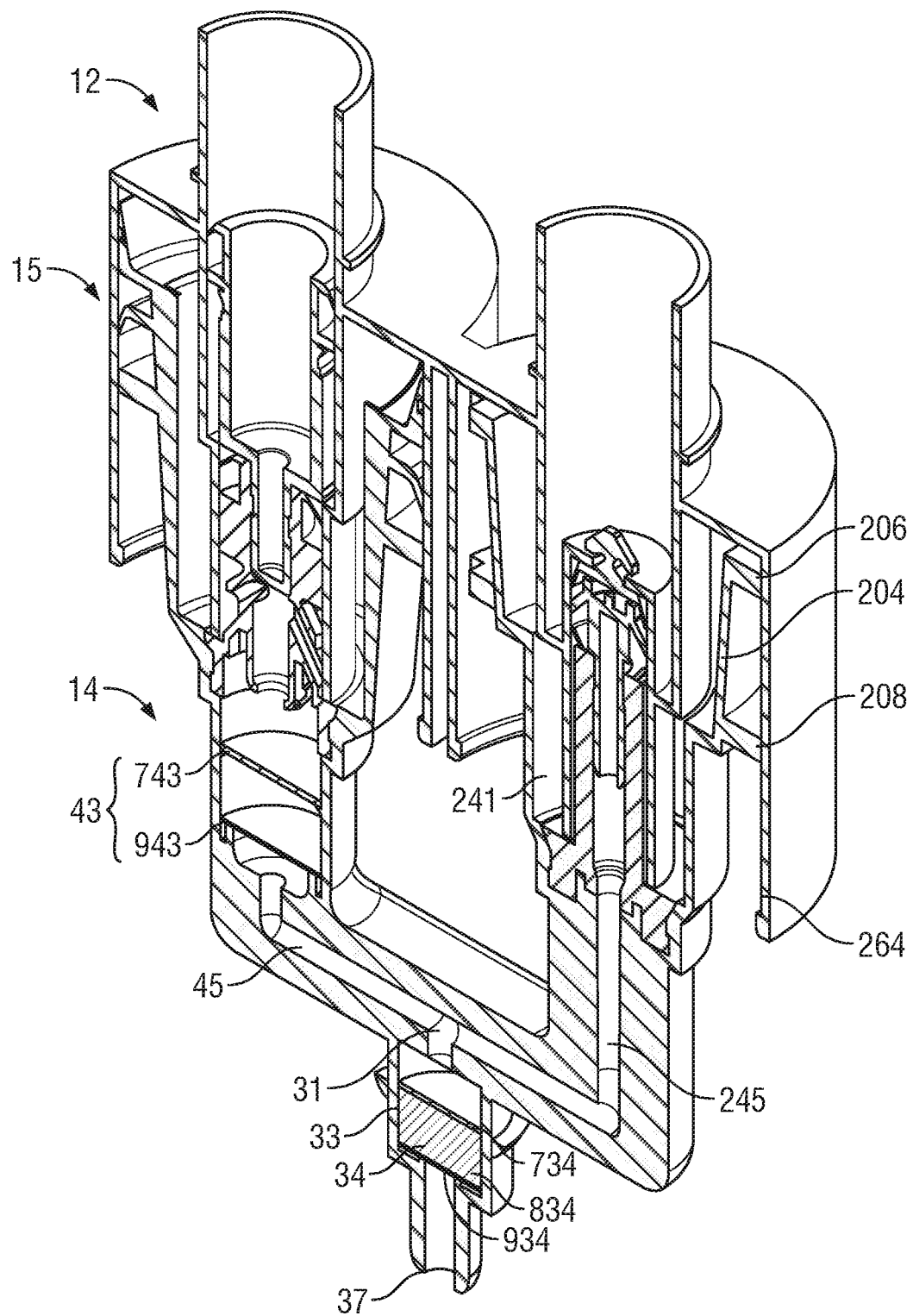
FIG. 9 is a cross-sectional front pictorial view of the pump assembly of FIG. 8 showing the piston-forming member in a retracted condition relative to the piston chamber-forming body similar to FIG. 3.

Reference is made to FIGS. 8 and 9 which illustrate a second embodiment of a pump assembly 12 for use in accordance with the present invention. In FIG. 8, the foam discharge arrangement 30 and the first foaming pump arrangement 40 are identical to that shown in the first embodiment of FIG. 6 with the exception of the modification of the foam inducing members 43 and 34. In FIGS. 8 and 9, there is substituted for the second foaming pump arrangement 140 of FIG. 6 a second liquid pump arrangement 240 having functional equivalence to a liquid pump as taught in U.S. Pat. No. 5,676,277 to Ophardt issued Oct. 14, 1997, the disclosure of which is incorporated herein by reference.

As seen in FIGS. 8 and 9, the second liquid pump arrangement 240 operates such that in a withdrawal stroke on moving the piston-forming element 14 relative the piston chamber-forming body 15 from the retracted position of FIG. 9 to the extended position of FIG. 8, the second liquid 124 is drawn from the second reservoir 116 and, in a retraction stroke from the extended position of FIG. 8 to the retracted position of FIG. 9, the second liquid 124 is discharged through a first discharge passageway 245 and into the mixing inlet passageway 31.

As a result of the simultaneous operation of the first foaming pump arrangement 40 and the second liquid pump arrangement 240 in a retraction stroke, the first liquid 24 and first air (as the first intermediate product 44) and the second liquid 124 are simultaneously passed into the mixing chamber 33 and forced through the outlet foam inducing member 34 to be discharge out the discharge outlet 37 as a final foamed product 239.

In the second embodiment of FIGS. 8 and 9 the second liquid pump arrangement 240 comprises a second liquid pump 241 with a second liquid piston 265 coaxially slidable within a cylindrical second liquid chamber 262. At an inner end, the second liquid chamber 262 has an opening, open to the reservoir 216. Across the opening a one way valve 201 is provided permitting flow merely outwardly is from the reservoir 216 into the second liquid chamber 262. The second liquid piston 265 is coaxially reciprocally slidable within the second liquid chamber 262. The piston 265 has a hollow stem 275 with a central passageway 276 there through leading to the second discharge passageway 245. The second liquid piston 265 carries an inner disc 266 which engages the second liquid chamber 262 to permit merely second liquid 124 to flow outwardly there past. The second liquid piston 265 carries an outer disc 267 which prevents fluid flow outwardly there past. A radially extending port 202 through the stem 275 between the inner disc 265 and the outer disc 266 permits fluid flow from an annular space between the inner disc 265 and the outer disc 266 radially through the stem 275 and to the central passageway 276. A second liquid compartment 268 is defined within the second liquid pump 241 between the one way inlet valve 201 and the inner disc 265. The volume of the liquid compartment 260 varies with axial movement of the second liquid piston 265 relative to the second liquid chamber 262. In retraction stroke, the second liquid 124 is forced passed the inner disc 265 through the port 202 and into the central passageway 276. In a withdrawal stroke, the volume of the second liquid compartment 268 increases and the second liquid 124 is drawn from the reservoir 116 into second the liquid chamber 262 past the one way valve 201.

In the second embodiment of FIGS. 8 and 9, coaxially about the second liquid piston 265 there is provided a guide piston 204 with two cylindrical guide web 206 and 268 for engagement with a cylindrical wall 264 to assist in coaxial location of the second liquid piston 265 within the second liquid chamber 262 with the guide rings 206 and 208 having axially extending openings to permit air to freely pass axially therepast.

In FIGS. 8 and 9 the outlet foam inducing member 34 comprises: an outer screen 934 proximate the outer end 35 of the outlet mixing chamber 33, an inner screen 734 closer to the inlet of inner end 32 the outlet mixing chamber 33 spaced inwardly from the outer screen 134 and a porous foam plug 834 between the outer screen 934 and the inner screen 734. In FIGS. 8 and 9, the first foam inducing member 43 comprises: an outer screen 943 proximate the outer end 35 of the first mixing chamber 53 and an inner screen 743 closer to the inlet of inner end of the first mixing chamber 53.

In a preferred method of operating the second embodiment of FIGS. 8 and 9, the first liquid 24 when passed through the first foam inducing member 43 with the first air provides the first intermediate product 44 as a foamed product. The second liquid 124 is delivered as a liquid to the foaming discharge arrangement 30. The foamed first intermediate product 44 is mixed with the unfoamed second liquid 124 in the outlet mixing chamber 33 and passed through the outlet foam inducing member 34 to provide the resultant final product 39. Having the second liquid 124 not pass through a foam inducing member before it is mixed with the first intermediate product 44 can be advantageous. The first embodiment as shown in FIGS. 2 to 7 may be operated in a not dissimilar manner to operation of the second embodiment with the first liquid 24 comprising a liquid which when passed through the first foaming pump arrangement 40 provides a first intermediate product 44 which is a foamed product, and the second fluid 124 comprising a liquid which does not produce foam when passed through the second foam generating member 140. However, nevertheless, when the first intermediate product 44 and the second intermediate product 144 or merely the second liquid 124 are passed through the foamed discharge arrangement 30, an advantageous final product 39 can be obtained as a foamed product having useful characteristics. As contrasted with the second embodiment of FIGS. 8 and 9, in the use of the first embodiment of FIGS. 2 to 7, even if the second liquid 124 may not foam when passed through the second foam inducing member 143, in the first embodiment there is provided to the foam discharging arrangement 30 the additional second air as is advantageous for product of the final product 39 as a foamed product. In the first embodiment in the situation that the second liquid 124 does not foam, the second foam inducing member 143 may be eliminated or modified so as to merely provide some reasonable mixing of the second liquid 124 and the second air.

Third Embodiment

Figure 10:
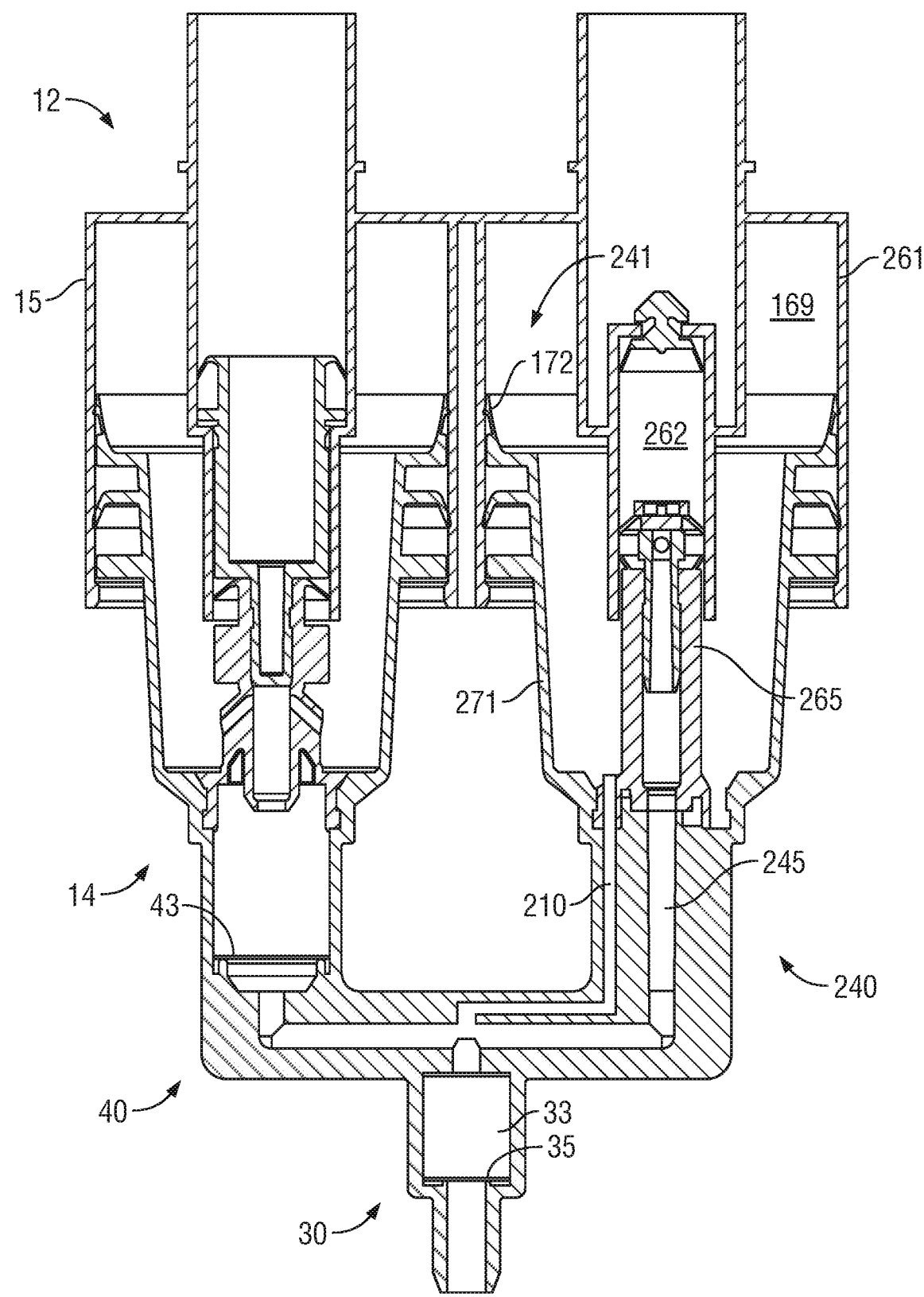
FIG. 10 is a cross-sectional front view of a third embodiment of a pump assembly in accordance with the present invention showing the piston-forming element in an extended condition relative to the piston chamber-forming body similar to FIG. 8.

Reference is made to FIG. 10 which is a cross-sectional front view of a third embodiment of a pump assembly 12 in accordance with the present invention showing the piston-forming element 14 in an extended condition relative to the piston chamber-forming body 15 similar to FIG. 8. In FIG. 10, the pump assembly 12 is identical to the pump assembly 12 in FIG. 8 with the notable exception that a second air pump 241 is provided by reason of the replacement of the guide piston 204 of FIG. 8 with a second air piston 271 having an inner disc 172 to engage the second air chamber wall 264 so as to provide an air compartment 169 whose volume varies with relative movement of the second air piston 271. The second air pump 241 is provided with an air discharge passageway 210 that delivers the second air to the outlet mixing chamber 33 independently of the second discharge passageway 245 that delivers the second liquid 124.

Fourth Embodiment

Reference is made to FIGS. 11 to 15 which illustrate a fourth embodiment of a pump assembly 12 in accordance with the present invention comprising a piston-forming element 14 reciprocally slidable relative to a piston chamber-forming body 15. In FIGS. 11 to 15, similar reference numbers are used as in the other embodiments to indicate similar elements.

Figure 13:
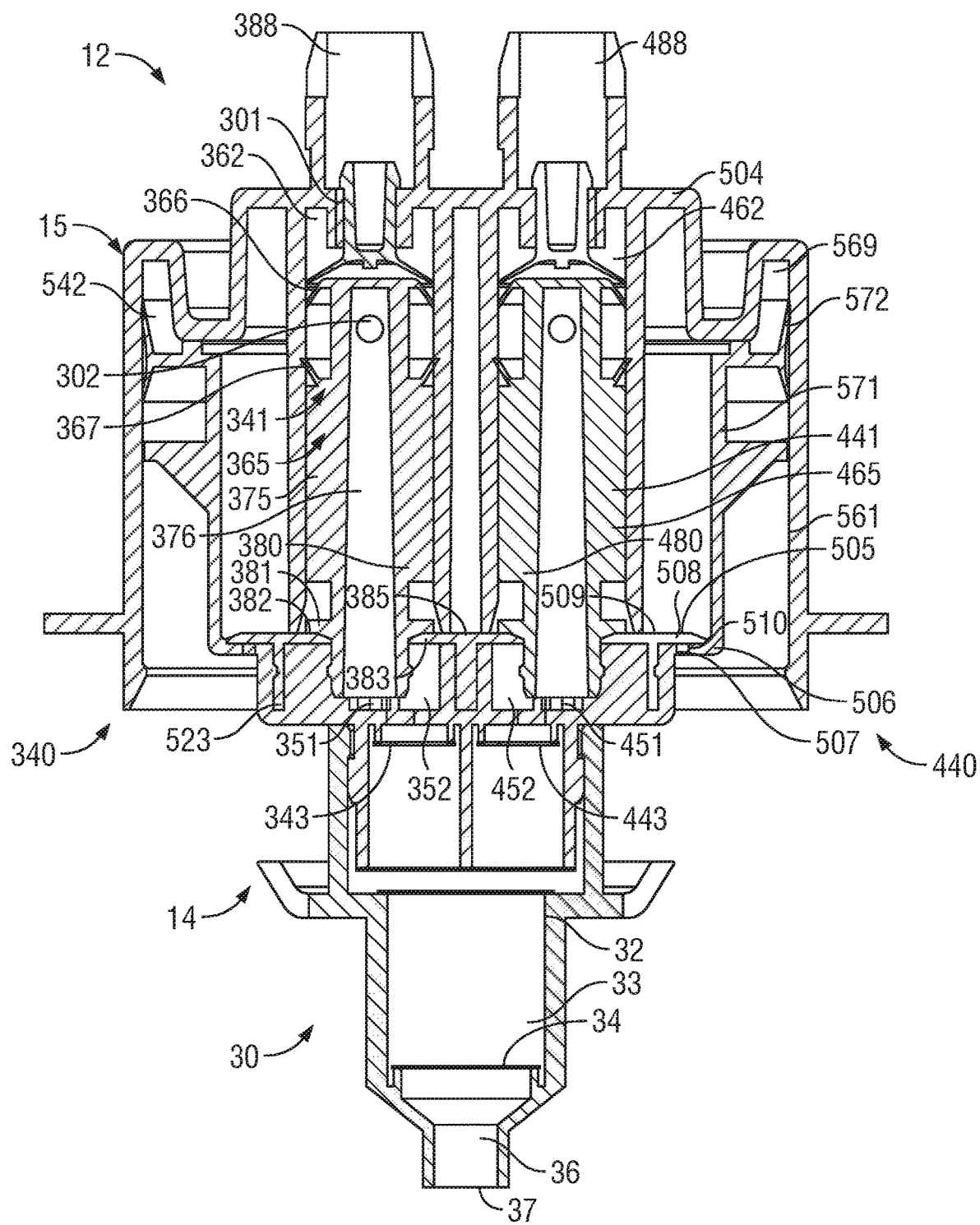
FIG. 13 is a cross-sectional front view of the pump assembly of FIG. 11 along section 4-4 in FIG. 11 with the piston-forming member in a retracted position relative to the piston chamber-forming body.

As seen in FIG. 13 schematically designated by the broken lines, the pump assembly 12 include the first foaming discharge arrangement 30, a first foaming pump arrangement 340 and a second foam pumping arrangement 440. The foaming discharge arrangement 30 comprises a mixing chamber 33 have an inner end 32 and a discharge passageway 36 leading from an outer end 35 to a discharge outlet 37. Proximate the outer end 35 of the mixing chamber 33 there is provided an outlet foam inducing member 34 shown as a screen.

The first foaming pump arrangement 340 and the second foaming pump arrangement 440 are identical mirror images of each other. The first foaming pump arrangement 340 includes a first liquid pump 341. The second foaming pump arrangement 440 includes a second liquid pump 441 the same as the first liquid pump 341. The first liquid pump 341 and the second liquid pump 441 are each substantially the same as the second liquid pump 241 shown on the second liquid pump arrangement 240 of FIGS. 8 and 9. Each of the first liquid pump 341 and the second liquid pump 441 have a functional equivalence to a liquid pump as taught by U.S. Pat. No. 5,676,277 to Ophardt issued Oct. 14, 1997.

The first liquid pump 341 has a first liquid piston 365 coaxially slidable within a cylindrical first liquid chamber 362 formed on the piston chamber-forming body 15. An inner end first liquid chamber 362 is open to a reservoir containing a first fluid 24 and a one-way valve 301 is provided permitting flow merely outwardly from the reservoir into the first liquid chamber 362. The first liquid piston 365 has a hollow stem 375 with a central passageway 376 therethrough leading to a first discharge outlet 351 into a first mixing chamber 352 with a first foam inducing member 343 across the lower end of the first mixing chamber 352. The first liquid piston 365 carries an inner disc 366 which engages the first liquid chamber 362 to merely permit the first fluid 24 to flow outwardly therepast. The first liquid piston 365 carries an outer disc 367 which prevents fluid flow outwardly therepast. A radially extending port 302 extends through the stem 375 between the inner disc 365 and the outer disc 366. In a retraction stroke, the first fluid 24 is forced passed the inner disc 366 through the port 302 and into the central passageway 376. In a withdrawal stroke, the first liquid 24 is drawn from the reservoir past the one way valve 301. The construction and operation of the second liquid pump 441 is the same as the first liquid pump 341 and elements of the second liquid pump 441 are referred to by similar reference numerals, however, identified as being 400 series rather than 300 series.

The piston chamber-forming body 15 and the piston-forming element 14 form an air pump 542 therebetween. The piston chamber-forming body 15 has an end wall 504 which carries the first liquid chamber 362 and the second liquid chamber 462 each disposed about parallel axes. The piston chamber-forming body 15 has a cylindrical outer air chamber wall 561 disposed about an axis parallel to the axes of the first liquid chamber 362 and the second liquid chamber 462. The piston-forming element 14 carries an air piston 571 radially outwardly from the first liquid piston 365 and the second liquid piston 465. The air piston 571 carries an inner disc 572 at an inner end which sealably engages with the outer air chamber wall 561 forming an air compartment 569 between the air piston 571 and the piston chamber-forming body 15. The air compartment 569 varies in volume with coaxial sliding of the piston-forming element 14 relative to the piston chamber-forming body 15. The air pump 542 carries a one way air inlet valve 505 which permits air flow from the atmosphere into the air compartment 569 but prevents fluid flow outwardly from the air compartment 569. In this regard, the air piston 571 has an axially inwardly directed shoulder 506 with spaced air inlet openings 507 through the shoulder 506 providing for communication of the air from the atmosphere into the air compartment 569. As can best be seen in FIG. 14, the one-way air inlet valve 505 comprise a radially outwardly extending annular disc 508 supported at a radial inner end 509 and presenting an axially outwardly directed sealing surface 510 which engages the inwardly directed shoulder 506 to form a seal therewith to prevent air flow from the air chamber 569 through the air inlet openings 507. The disc 508 deflects axially inwardly to permit atmospheric air to flow through the air inlet opening 207 into the air compartment 569 as when a vacuum condition is created within the air compartment 569. The air compartment 569 includes a pair of one way air outlet valves, namely, a first one-way air outlet valve 380 providing for air flow from the air compartment 369 into the first mixing chamber 352 and a second one-way air outlet valve 480 permitting air flow form the air compartment 569 into the second mixing chamber 452.

The first liquid piston 365 includes axially inwardly of the first mixing chamber 353 a radially outwardly extending annular flange 381 with an axially outwardly directed seat shoulder 382. A resilient annular disc 383 is provided coaxially about the stem 375 immediately axially outwardly from the flange 381 with a central opening 384 of the disc 383 coaxially about the stem 375. The disc 383 carries a radially outer edge 385 that is secured against movement and sealed to prevent flow therepast. The disc 383 carries an axially inwardly directed sealing surface for engagement with the seat shoulder 382 of the flange 381 to prevent flow of air and/or liquid axially inwardly therepast. The disc 383 is resiliently deflectable axially outwardly away from the seat shoulder 382 to permit air flow axially outwardly from the air compartment 569 into the first mixing chamber 352. The second one way air outlet valve 480 is an identical mirror image of the first one way air outlet valve 380.

In a retraction stroke of the piston forming element 14, the air pump 542 pressurizes the air compartment 569 closing the one-way air inlet valve 505 and opening both the first one-way outlet valve 380 and the second one-way outlet valve 480 forcing air into the first mixing chamber 352 and the second mixing chamber 452 simultaneously with the first liquid pump 341 discharging liquid via the discharge outlet 351 into the first mixing chamber 352 and the second liquid pump 441 discharging liquid via the discharge outlet 451 into the second mixing chamber 452. The first liquid 24 and the first air pass through the first foam inducing member 343 providing a first intermediate product to the final mixing chamber 33. The second liquid 124 and the second air through the second foam inducing member 443 providing a second intermediate product to the mixing chamber 33. The first intermediate product and the second intermediate product are then simultaneously passed through the outlet mixing chamber 33, the outlet foam inducing member 35 and discharged as a final product out the discharge outlet 37.

In the fourth embodiment, in effect a single air pump 542 is provided comprising the single air compartment 569 from which the two one way air outlet valves 383 and 483 provide separate flows of air to each of the first mixing chamber 352 and the second mixing chamber 452.

In the fourth embodiment, in one preferred method of operation, an inlet 388 to the first liquid chamber 362 is connected to a first reservoir containing the first fluid 24 and an inlet 488 of the second liquid pump 441 is connected to a second reservoir containing the second liquid 124. This is not necessary and both inlets 388 and 488 may be connected to the same reservoir as for example in the situation that the same fluid may be desired to be passed through both the first pump 341 and the second pump 441.

Figure 12:
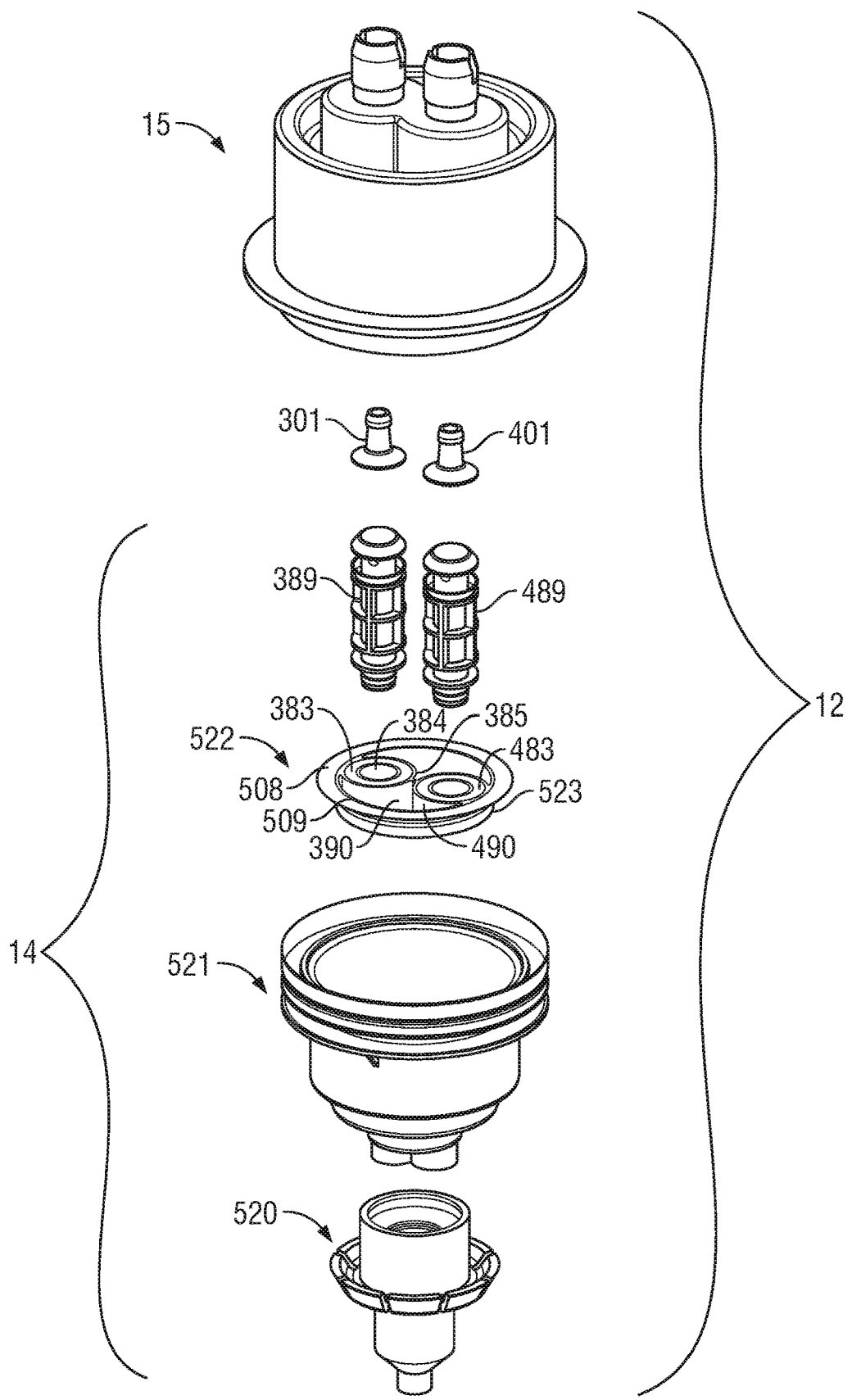
FIG. 12 is a pictorial exploded view of a pump assembly of FIG. 11.

Reference is made to FIG. 12 which illustrates an exploded view of the components of the pump assembly 12. The piston chamber-forming body 15 is shown as a unitary member as preferably injection molded from plastic into which the two one-way valves 301 and 401 each preferably a resilient member are to be secured as in a snap fit. The piston-forming element 14 is shown as comprising four parts, namely a nose portion 520, a bell portion 521, a valving member 522, a first piston element 389 and a second piston element 489. As can be seen from FIGS. 12 to 15, the valving member 522 has a cylindrical annular outer tube 523 which sealably engages in a snap fit in an annular slot 524 in a base of the bell portion 521 and with a pair of inner cylindrical tubes 390 and 490 supported by the outer tube 523.

An upper portion of the first mixing chamber 352 opens upwardly and is formed within an axially inwardly extending first inner cylindrical wall ending at an inner distal end. A plurality of circumferentially spaced axially extending and radially inwardly extending holding vanes 391 extend from the inside of the first inner cylindrical wall towards the center of the first inner cylindrical wall and define a central recess within which an outer end of the first piston element 389 is fixedly engaged as in a snap fit coaxially. The inner cylindrical tube 390 is sealably engaged coaxially about the first inner cylindrical wall. The disc 383 has its outer edge 385 secured to an axially inner end of first inner cylindrical wall and the disc 383 extends radially inwardly from axially inner end of first inner cylindrical wall to its central opening 384 coaxial about the stem 375 of the first liquid piston 365, axially outwardly of the seat shoulder 382 of the flange 381 on the stem 375. The upper portion of the first mixing chamber 352 within the first inner cylindrical wall is supported on a radially extending end wall which also supports a first outer cylindrical tube opening outwardly and forming an outer portion of the first mixing chamber 352 within which the first foam inducing member 343 is supported. An axially extending first port is provided through the end wall into the first outer cylindrical tube to provide communication between the upper portion of the first mixing chamber 352 and the lower portion of the first mixing chamber 352.

Similarly, an upper portion of the second mixing chamber 452 opens upwardly and is formed within an axially inwardly extending second inner cylindrical wall ending at an inner distal end. A plurality of circumferentially spaced axially extending and radially inwardly extending holding vanes 491 extend from the inside of the second inner cylindrical wall towards the center of the second inner cylindrical wall and define a central recess within which an outer end of the second piston element 489 is fixedly engaged as in a snap fit coaxially. The inner cylindrical tube 490 is sealably engaged coaxially about the second inner cylindrical wall. The disc 483 has its outer edge 485 secured to an axially inner end of second inner cylindrical wall and the disc 483 extends radially inwardly from axially inner end of second inner cylindrical wall to its central opening 484 coaxial about the stem 475 of the first liquid piston 465, axially outwardly of the seat shoulder 482 of the flange 481 on the stem 475. The upper portion of the second mixing chamber 452 within the second inner cylindrical wall is supported on a radially extending end wall which also supports a second outer cylindrical tube opening outwardly and forming an outer portion of the second mixing chamber 452 within which the second foam inducing member 443 is supported. A second axially extending port is provided through the end wall into the second outer cylindrical tube to provide communication between the upper portion of the second mixing chamber 452 and the lower portion of the second mixing chamber 452.

The provision of the resilient components of each of the one-way air inlet valve 505 and the two one-way air outlet valves 380 and 480 on the same valving member 522 reduces the number of elements required for the pump assembly 12.

The fourth embodiment illustrates an arrangement in which two liquid pumps 341 and 441 are operative with separate mixing chambers. Separate air outlets deliver air from the air pump 542 to the separate mixing chambers for each of the two liquid pumps to which the liquid from each pump is also delivered. In the fourth embodiment the two liquid pumps 341 and 441 are located centrally of an air piston 571 of the air pump 542 within an air chamber for the air pump 542 as is convenient for delivery of air to each of the separate mixing chambers for each of the two liquid pumps. The fourth embodiment illustrates an arrangement in which two liquid pumps 341 and 441 are operative with separate mixing chambers and with two separate air outlets delivering air from the air pump 542 to the separate mixing chambers for each of the two liquid pumps to which the liquid from each pump is also delivered. The fourth embodiment may be modified such that the second pump 441 may have its mixing chamber and the air delivery outlet for the second pump eliminated such that the second pump delivers merely the second liquid and not air.

While the fourth embodiment illustrates an arrangement with two liquid pumps, three or more such pumps may similarly be provided within air piston 571 of the air pump 542. The air from the single air pump 542 may be delivered to but one or more of the mixing chambers of the liquid pumps.

Foam Inducing Member

The preferred embodiments illustrate the use as a foam inducing member of a screen. The particular nature of the foam inducing member is not limited. Preferred foam inducing members have relatively small openings through which a liquid and air are forced to produce foam. The foam inducing member may comprise, for example, a screen of plastic or metal; a mesh; a batting a bonded fibres, a porous body formed as by sintering; and a porous form of plastic material, for example, open celled foamed plastics. The foam inducing member preferably generates turbulence in the fluid passing there through to generate foam when air and a liquid are simultaneously passed through the porous member.

In the first embodiment of FIG. 6, the outlet foam inducing member 34 is a single screen. However, the outlet foam inducing member 34 may comprise a number of foam inducing elements. For example, as in FIG. 8 in addition to the outlet foam inducing member 34 comprising two spaced screens 934 and 734 with a porous plug 834 between them, one or more of the screen 934, the plug 734 and the screen 734 may be eliminated.

Similarly, the first embodiment of FIG. 6 the first foam inducing member 43 is a single screen. However, the first foam inducing member 43 may comprise one or more foam inducing elements such as described above in respect of the outlet foam inducing member 34, for example as a pair of spaced screens as one or more screens, and as including one or more porous plugs.

The second foam inducing member 143 of the second foaming pump arrangement 140 may be identical to the first foam inducing member 43, however, may also be different. The first foam inducing member 43, the second foam inducing member 143 and the outlet foam inducing member 34 may each be the same or similar or different. Each should be suitably selected having regard, for example, up to a number of features including the desired characteristics of the resultant final product 39 and achieving such desired characteristics having regard to the nature of the first liquid 24 and the second liquid, the first intermediate product 39, and the second intermediate product 139.

Feature Selection

The configuration of the pump assembly 12 permits a number of features of the pump assembly to be selected. The present invention and the preferred embodiment of the pump assembly 12 disclosed advantageously provide opportunities for adjusting parameters of the dispenser 10 and its method of operation so as by simple experimentation to determine advantageous configurations to produce a final product with advantageous foam characteristics for cleaning. Variables which can be selected include amongst others:

A. The nature of each of the foam inducing members 33, 43 and 143;

B. The ratio of the volume of the first liquid 24 to the second liquid 124;

C. (i) The ratio of the volume of the first liquid 24 to the first air; and (ii) the ratio of the volume of the second liquid 124 to the second air;

D. (i) The nature of the first liquid 24 and its additives; and (ii) the nature of the second liquid 124 and its additives.

A. Foam Inducing Members

The configuration of the pump assembly 12 permits the selection of the foam inducing members including the first foam inducing member 43, the second foam inducing member 143 and the outlet foam inducing member 34 to be selected to develop advantageous foaming for each of the first intermediate product 44, the second intermediate product 144 the foam product 39.

B. Liquid/Liquid Ratio

The configuration of the pump assembly 12 permits the selection as to the relative volume of the first liquid 24 that is dispensed in each cycle compared to the volume of second liquid 124 that is dispensed in each cycle.

In the preferred embodiment illustrated in FIG. 6 with the first foaming pump arrangement 40 and the second foaming pump arrangement 140 indicated as being identical, in each cycle of operation the volume of the first liquid 24 discharged and the volume of the second liquid 124 dispensed will be equal. This is not necessary and, in many applications, it will be advantageous to have the volume of the first liquid 24 discharged in a cycle different than the volume of the second liquid 124 discharged in a cycle having regard to the nature of the liquids being used. For example in the case that the first liquid is the same as the second liquid the second foaming pump arrangement 140 may liquid discharge a different volume of the second liquid 124 than the volume of the first liquid 24 discharged. Preferably, the volume of the first fluid 24 discharged in a stroke is in a range of ¼ to 4 time the volume of the second fluid 124 discharged.

C. Liquid/Air Ratio

The configuration of the pump assembly 12 permits the selection as to the relative volume of the first liquid 24 that is dispensed in each cycle compared to the relative volume of the first air that is dispensed in each cycle. The configuration of the pump assembly 12 permits the selection as to the relative volume of the second liquid 124 that is dispensed in each cycle compared to the relative volume of the second t air that is dispensed in each cycle.

The ratio of the volume of the first liquid 24 to the first air (at atmospheric pressure) is preferably selected having regard to the nature of the first liquid 24 so as to provide an advantageous ratio for the first intermediate product 44 to have a desired foam consistency. The ratio of volumes of the first liquid 24 to the first air may vary widely. Preferably, the volume of the first air (said atmospheric pressure) is in the range of 5 to 25 times volume of the first liquid 24; for example, preferably in the range of about 10 to 25 times, more preferably, in the range of about 10 to 15 times, advantageously 15 times, particularly when the first liquid comprises an alcohol and water composition containing at least 40% volume of alcohol by volume.

Preferably, the volume of the second air (said atmospheric pressure) is in the range of 5 to 25 times volume of the second liquid 124; for example, preferably in the range of about 10 to 25 times, more preferably, in the range of about 10 to 15 times, advantageously 15 times, particularly when the second liquid comprises an alcohol and water composition containing at least 40% volume of alcohol by volume.

In the preferred embodiment illustrated in FIG. 6 with the first foaming pump arrangement 40 and the second foaming pump arrangement 140 indicated as being identical, in each cycle of operation, the volume of the first air discharged and the volume of the air dispensed will be equal. This is not necessary and, in many applications, it will be advantageous to have the volume of the first air discharged in a cycle different than the volume of the second air discharged in a cycle. As well, the second foaming pump arrangement 140 may discharge the second liquid 124 in a different relative volume to the second air than the relative volume of the first liquid 140 to the first air.

D. Nature of the Two Liquids

The dispenser in accordance with the present invention permits the selection of the first liquid 24 and the second liquid 124. The first liquid 24 may be the same as the second liquid 124 or the first liquid 24 may be different than the second liquid. 124.

i: Same Liquids

The first liquid can be selected to be the same as the second liquid. Operation of the first embodiment of the dispenser 10 with the first fluid 24 identical to the second fluid 124 identical has a number of advantages.

Towards developing comparison test data, a dual dispenser in accordance with this invention having a configuration similar to that of the first preferred embodiment shown and including a first foaming pump arrangement, a second foaming arrangement and a foaming discharge arrangement is used to produce from a first liquid and a second liquid, a final dual product. For comparison, a test dispenser is configured to be identical to the dual dispenser but with the second foaming pump arrangement eliminated by being disabled, such that the test dispenser comprises merely the first foam pump arrangement and the foaming discharge arrangement. In a first test procedure, a test liquid is passed through the test dispenser to dispense a final test product from the discharge outlet. The final test product is compared to the final dual product.

As a first example and method of operation in accordance with the present invention, the first liquid 24 and the second fluid 124 are selected to both be the same commercially available water and alcohol first test mixture which normally produces foam when passed through a typical foam generator, and these two liquids are passed through the dual dispenser to produce the final dual product. The same water and alcohol first test mixture was passed through the first test dispenser to produce a test final product. The test product was a foamed products with reasonable foam characteristics for hand cleaning. The final dual product also was a foamed product with reasonable foam characteristics for hand cleaning, however, the dual product had different foam characteristics than the foam characteristics of the test product. The dual product has superior foam characteristics for hand cleaning than the test product, for example, by including smaller foam bubbles, more consistent foam, and more stable foam. The foam of the test product foam did not have as advantageous properties as the foam of the dual product. It is believed that in the dual dispenser in accordance with the present invention the mixing of the foamed intermediate products, that is, the first intermediate product 44 and the second intermediate product 144 in the mixing chamber 33 and their subsequent passage through the outlet foam inducing member 37 enhances dispersion of air within the liquids and results in smaller air bubbles a more consistent foam characteristics of the dual foam product.

As a second example and method of operation in accordance with the present invention, the first liquid and the second fluid are selected to both be the same commercially available liquid soap and water second test mixture which normally produces foam when passed through a typical foam generator, and these two liquids are passed through the dual dispenser to produce the final dual product. The same liquid soap and water second test mixture was also passed through the first test dispenser to produce a test final product. The test product was a foamed products with reasonable foam characteristics for hand cleaning. The final dual product also was a foamed product with reasonable foam characteristics for hand cleaning, however, the dual product had different foam characteristics than the foam characteristics of the test product. The dual product has superior foam characteristics for hand cleaning than the test product, for example, by including smaller foam bubbles, more consistent foam, and more stable foam. The foam of the test product foam did not have as advantageous properties as the foam of the dual product. It is believed that in the dual dispenser in accordance with the present invention the mixing of the foamed intermediate products, that is, the first intermediate product 44 and the second intermediate product 144 in the mixing chamber 33 and their subsequent passage through the outlet foam inducing member 37 enhances dispersion of air within the liquids and results in smaller air bubbles a more consistent foam characteristics of the dual foam product.

ii: Different Liquids

The first liquid 24 may be selected to be different than the second liquid 124. Operation of the first embodiment of the dispenser 10 with the first fluid 24 different than the second fluid 124 has a number of advantages.

As a third example and method of operation in accordance with the present invention, the first liquid 24 is a commercially available mixture of alcohol and water which foams when passed through the first foaming pump arrangement 40 of the dual dispenser to produce the first intermediate product 44 as a foam. The second liquid 125 is a commercially available mixture of liquid soap and water which produces foam when passed through the second foaming pump arrangement 140 of the dual dispenser to produce the second intermediate product 145 as a foam. Surprisingly, when such first intermediate product 44 comprising a foamed alcohol and water mixture and the second intermediate product 144 comprising the foam liquid soap and water mixture are passed through the foaming discharge arrangement 30 of the dual dispenser in accordance with the present invention, a resultant dual product is provided which is a foamed product having foam with characteristics suitable for hand cleaning however not as good foam characteristics as the best of either first intermediate product 44 or the first intermediate product 44. The dual product, however, has advantageous cleaning properties in comprising a mixture of alcohol, soap and water. In one aspect the present invention provides such a foamed dual product including air, alcohol, liquid soap and water, and a method of producing the same with a dual dispenser in accordance with the present invention.

As a fourth example and method of operation in accordance with the present invention, the first liquid 24 is selected as a first mixture of soap and water and the second liquid 124 is a second mixture of soap and water different than the first mixture of soap and water. The second mixture differs from the first mixture as to any manner of features, including the nature of the soap(s), the relative weight/volume of the soap(s), and the nature and/or relative amounts of different additives including, for example, foaming agents, foam stabilizing agents, surfactants, skin moisturizers, fragrances and the like.

As a fifth example and method of operation in accordance with the present invention, the first liquid 24 is a first alcohol and water composition and the second liquid 124 is a second alcohol and water composition different than the first alcohol and water composition. The second alcohol and water composition differs from the first alcohol and water composition as to any manner of features, including the nature of the alcohol(s), the relative volume of the alcohol(s), and the nature and/or relative amounts of different additives including, for example, foaming agents, foam stabilizing agents, surfactants, skin moisturizers, fragrances and the like.

As a sixth example and method of operation in accordance with the present invention, as the first fluid, a commercially available cleaning composition is selected that comprises alcohol and water and includes additives that ensure that when the cleaning composition is passed through the test dispenser, a test product is dispensed that is a foam product with advantageous cleaning properties. The second liquid is selected to be this same commercially available cleaning composition but modified to decrease the additives to an amount such that when the second fluid is passed through the test dispenser a test product is dispensed that has but marginal foaming. Such first fluid and second fluid are passed through the dual dispenser in accordance with the present invention and the dual product obtained is a foam product with improved quality compared to the test product.

In a the seventh example and method of operation in accordance with the present invention, a commercially available base cleaning composition is selected that comprises water and alcohol, for example, 30% to 40% by volume of the volume of the composition, and includes a foaming agent in a base amount that ensures that when such cleaning composition the is passed through the test dispenser a test product is dispensed as a foam product with advantageous cleaning properties. The first liquid 24 is selected to be the base cleaning composition however modified to increase the amount of foaming agent from the base amount by an excess amount. The excess amount is selected to be an amount which assists when the first intermediate product 44 and the second intermediate product liquid 144 are passed through the foaming discharge arrangement 30, in producing the dual product as a foam product. The second liquid is selected to be an alcohol and water composition that comprises alcohol in a greater % than the first liquid, for example 40% to 90% by volume of the volume of the composition, and no foaming agent, or small amounts of a foaming agent such that when the second liquid is passed through the test dispenser the test product is a product that is not a foam product or a partially or poorly foamed product. When the first liquid and the second liquid are passed through the dual dispenser a dual product is discharges as a foam product with advantageous cleaning properties.

In the seventh example, the excess amount of the foaming agent can be selected, for example, as amount of the foaming agent required to dispense from the test dispenser a test product that is a foam product by mixing the first liquid and the second liquid as liquids in a volume ratio that they are dispensed through the dual dispenser. The sixth example can be used to avoid proprietary compositions which restrict proportions of ingredients based on volume % of the total composition by selecting the first liquid and the second liquid to avoid the proprietary compositions and ensuring that with the addition of the first air and any the second air that any compositions in the foaming discharge arrangement 30 are different than the proportions of ingredients in proprietary compositions.

The use of the first liquid 24 with higher than normal as, for example, double the foaming agents can produce a highly foamed first intermediate product 44 which when mixed with the second intermediate product 144 will provide an advantageous foam characteristics to the dual product even when the second intermediate product 144 may not be a foam, or if a foam does not have advantageous characteristics for hand cleaning. In this seventh example as one preferred scenario, the first liquid 24 is a mixture of 35% by volume alcohol to the total composition with the balance being water and a foaming agents in an amount of the base amount plus an excess amount of 1 to 3 times base amount, and the second liquid 124 in a volume equal to that of the first liquid, and comprising 70 to 90% by volume alcohol with a balance being water and no foaming agent. The first liquid 24 in passing through the first foaming pump arrangement 40 provides the first intermediate product as a foam while the second liquid provides the second intermediate product 144 as a product that is not foam or only partially foamed. However, when such first intermediate product 44 and the second intermediate product 144 are passed through the foaming discharge arrangement 30 of the dual dispenser the dual product has advantageous foam characteristics for hand cleaning.

An eighth example and method of operation in accordance with the present invention is the same as the seventh example, however, in which the base composition includes a stabilizing agent and or other additives in a base amount in the range if 1 to 3 times the base amount. The second liquid is to not include the stabilizer or other additives or not to include the stabilizer or other additives up to the base amount. The excess amount of the stabilizer is selected such when the first intermediate product 44 and the second intermediate product liquid 144 are passed through the foaming discharge arrangement 30, the dual product to stabilize the dual product. The excess amount of the stabilizing agent can be selected, for example, as amount of the stabilizing agent required to produce by passing through the test dispenser a test product that is a stabilized foam by mixing the first liquid and the second liquid as liquids in a volume ratio that they are dispensed through the dual.

General

The preferred dispenser 10 in FIG. 1 illustrated the preferred pumping assembly 12 to dispense the final product 39 downwardly from the dispenser onto the user's hand 620. However, many other pump assemblies may be utilized, for example, to discharge product upwardly from a reservoir such as for example utilizing as both the first foaming pump arrangement 40 and the second foaming pump arrangement 140 two foam dispensing pumps as taught by U.S. Pat. No. 5,271,530 to Eurira et al.

The preferred embodiments illustrative the pump assembly 12 in which both the first foaming pump arrangement 40 and the second foaming pump arrangement 140 as well as the second liquid pump arrangement 240 comprise piston pumps. This is not necessary and various other forms of pumps may be used without limitation to discharge the liquids and/or the liquids and air in substitution of each of the pump arrangements disclosed in the preferred embodiments.

The preferred first embodiment as shown in the FIGS. 2 to 7 illustrates the use of a first foaming pump arrangement 40 having a configuration as disclosed in the above-noted U.S. Pat. No. 8,272,539. Such an arrangement provides the first liquid pump 41 to be out of phase with the first air pump 42 such that in a withdrawal stroke, air is drawn by the air pump 42 into a variable volume air compartment from the atmosphere through the discharge outlet 37; and, the first liquid 24 is discharged by the liquid pump 41 into the air compartment; and in a retraction stroke, the first liquid 24 is drawn by the liquid pump 41 into a variable volume liquid compartment and the first air and the first liquid 24 within the air compartment are discharged through the first discharge passageway 45. The use of out of phase pumps is not necessary and piston pumps may be used as in the fourth embodiment of FIGS. 11 to 15 in which each air pump and a liquid pump are in phase.

The first reservoir 16 and the second reservoir 116 are each preferably collapsible, however, need not be collapsible and may be vented or otherwise a mechanism may be provided to permit air to enter each chambers 18 and 118 to prevent a build of vacuum in either chamber which could prevent the dispensing of liquid from the chamber. In the preferred embodiment, the reservoir assembly 13 is shown as an integral member which can be made as by molding as one piece as can assist in handling of the cartridge 10, however, this is not necessary. Each of the first reservoir 16 and second reservoir 116 may comprise separate elements. In the preferred embodiment, the reservoirs are shown to be mirror images of each other and to have the same volume. This is not necessary and, for example, the reservoirs may have different volumes.

In both the first preferred embodiment and the second preferred embodiment, piston pumps are utilized and a single piston 14 is provided which incorporates the two pistons for the two pump arrangements, plus their discharge outlets, their mixing chambers, their foam inducing members, and discharge passageways as well as the foaming discharge arrangement 30 including the outlet mixing chamber 33, the outlet foam inducing member 37 and the discharge outlet 36. The single piston 14 in effect forming with the outlet passageways 44 and 144 and the mixing inlet passageway 34 an outlet manifold for the two piston pump arrangements. Having the piston 12 mechanically couple the pistons for the first foaming pump assembly 30, the second foaming pump assembly 31 and/or the second liquid pump assembly provides a convenient arrangement for manufacture and permits a single activator such as the lever 88 in FIG. 1 to engage the piston 14 and reciprocally move it relative to the piston chamber forming body 15 driving the two pump arrangements simultaneously.

The hand cleaner foam dispenser 600 illustrated in FIG. 1 shows an arrangement in which the cartridge 10 is adapted for use in a manually operated dispenser. A cartridge 10 as disclosed in accordance with the present invention is readily adapted for use with automatic soap dispensers such as the motor driven touchless dispensers shown in U.S. Pat. No. 8,622,243 to Ophardt et al. issued Jan. 7, 2014 and U.S. Pat. No. 8,733,596 to Ophardt et al. issued May 27, 2004, the disclosures of which are incorporated herein by reference.

The present invention has disclosed first, second and third embodiments each of which have two pump arrangements, 40 and 140, discharging two respective liquids 24 and 124 into the foam discharging arrangement 30. It is within the scope of the present invention to provide a third, fourth or more such pump arrangements. While not necessary, the pump arrangements may all be mechanically coupled to the foam discharge arrangement 30 with the arrangement 30 providing an effective discharge manifold for the pump arrangements. In the case that the pump assembly comprises a piston pump assembly 12 as in the preferred embodiments, each of the first pump arrangement, second pump arrangement, third pump arrangement and any additional pump arrangements can be disposed side by side with each disposed for sliding about parallel axes.

In accordance with the present invention there is delivered to the foaming discharge arrangement 30 the first intermediate product 44 preferably as a foamed product and one or more of: (a) the second intermediate product 144 as a foam product, (b) the second liquid 124 as a liquid, and (c) the second air as a separate air stream. In the preferred embodiments, all these input streams to the foam discharge arrangement 30 are shown as passing through and being mixed in the mixing passageway 32. It is within the scope of this invention to deliver these different inputs to the foam discharge arrangement 30 at different locations as for example at different radial or axial locations in the mixing chamber 33 and to discharge axially or radially or tangentially about an axis of the mixing chamber 33 into the mixing chamber 33.

While the invention has been described with reference to preferred embodiments, many variations and modifications will occur to these skilled in the art and for a definition of the invention reference is made to the claims.

We claim:

1. A method of operation of a hand cleaner foam dispenser to dispense a foamed mixture, the method comprising providing the dispenser comprising:

a first reservoir containing a first fluid;

a first pump arrangement operative to draw the first fluid from the first reservoir and to draw first air from the atmosphere and to simultaneously discharge the first fluid and the first air through a first foam inducing member into a final mixing chamber;

a second reservoir containing a second fluid;

a second pump arrangement operative to draw the second fluid from the second reservoir and to draw second air from the atmosphere and to simultaneously discharge the second fluid and the second air through a second foam inducing member into the final mixing chamber;

the final mixing chamber open to a discharge outlet via an outlet passageway; and an outlet foam inducing member across the outlet passageway, the method further comprising:

operating the first pump arrangement to draw the first fluid from the first reservoir and to draw the first air from the atmosphere and to simultaneously discharge the first fluid and the first air through the first foam inducing member into the final mixing chamber, operating the second pump arrangement to draw the second fluid from the second reservoir and to draw the second air from the atmosphere and to simultaneously discharge the second fluid and the second air through a second foam inducing member into the final mixing chamber, operating the first pump arrangement and the second pump arrangement to simultaneously discharge the first fluid and the first air through the first foam inducing member into the final mixing chamber and the second fluid and the second air through the second foam inducing member into the final mixing chamber, forcing the flow of the first fluid, the first air, the second fluid and the second air simultaneously from the final mixing chamber through the outlet foam inducing member and out the discharge outlet as a final product onto a person's hand, providing as the first fluid a first alcohol and water solution with not greater than 40% v/v alcohol and providing as the second fluid a second alcohol and water solution with greater than 40% v/v alcohol, and selecting (a) a relative volume of the first alcohol to water in the first fluid, (b) a relative volume of the second alcohol to water in the second fluid, (c) a volume of the first fluid discharged into the final mixing chamber, and (d) a volume of the second fluid discharged into the final mixing chamber compared to the volume of the first fluid discharged into the final mixing chamber such that in the final product discharged from the final mixing chamber through the outlet foam inducing member and out the discharge outlet has a volume ratio of alcohol to water greater than 40:60;

including providing the first fluid to include a first foaming agent, the first foaming agent provided in the first fluid comprises a base amount plus an additional excess amount, the base amount being an amount of the first foaming agent required to foam the first fluid as it passes through the first foam inducing member, wherein the excess amount of the first foaming agent is sufficient to foam the second fluid if the second fluid included the excess amount of the first foaming agent when the second fluid is passed through the second foam inducing member.

2. A method as claimed in claim 1 wherein the first fluid is selected to be a liquid which when discharged with the first air through the first foam inducing member produces a first foam.

3. A method as claimed in claim 1 wherein the first fluid is selected to be a liquid which when discharged with the first air through the first foam inducing member produces a first foam and the second fluid is a liquid which when discharged with the second air through the second foam inducing member does not produce a second foam.

4. A method as claimed in claim 1 wherein the first pump arrangement and the second pump arrangement are configured and operated such that at atmospheric pressure a volume of the first air is in the range of 5 to 20 times the volume of the first fluid and at atmospheric pressure a volume of the second air is in the range of 5 to 20 times the volume of the second fluid, and the volume of the first fluid is in the range of ¼ to 2 times the volume of the second fluid.

5. A method as claimed in claim 1 wherein selecting (a) the relative volume of the first alcohol to water in the first fluid, (b) the relative volume of the second alcohol to water in the second fluid, (c) the volume of the first fluid discharged into the final mixing chamber, and (d) the volume of the second fluid discharged into the final mixing chamber compared to the volume of the first fluid discharged into the final mixing chamber such that in the final product discharged from the outlet the volume ratio of alcohol to water is greater than 60:40.

6. A method as claimed in claim 1 including providing the first fluid to include a first foam stabilizing agent provided in the first fluid to comprise a base amount plus an additional excess amount, the base amount of the first foam stabilizing agent being an amount of the first foam stabilizing agent required to stabilize a first foam produced by the first fluid as it passes through the first foam inducing member, wherein the excess amount of the first foam stabilizing agent is sufficient to stabilize foam produced from the second fluid if the second fluid included the excess amount of the first foam stabilizing agent when the second fluid is passed through the second foam inducing member.

7. A method as claimed in claim 1 wherein the second fluid contains no foaming agents.

8. A method as claimed in claim 1 wherein the excess amount of the first foaming agent is 1 to 3 times the base amount.

9. A method as claimed in claim 1 wherein the first fluid comprises an alcohol and water solution with 30% to 40% by volume alcohol.

10. A method as claimed in claim 8 wherein the second fluid comprises an alcohol and water solution with 70% to 90% by volume alcohol.

11. A method as claimed in claim 9 wherein the second fluid comprises an alcohol and water solution with 70% to 90% by volume alcohol.

12. A method as claimed in claim 11 wherein the excess amount of the first foaming agent is 1 to 3 times the base amount.

13. A method as claimed in claim 5 wherein the second fluid contains no foaming agents.

14. A method as claimed in claim 5 wherein the excess amount of the first foaming agent is 1 to 3 times the base amount.

15. A method as claimed in claim 5 wherein the first fluid comprises an alcohol and water solution with 30% to 40% by volume alcohol.

16. A method as claimed in claim 5 wherein the second fluid comprises an alcohol and water solution with 70% to 90% by volume alcohol.

17. A method as claimed in claim 15 wherein the second fluid comprises an alcohol and water solution with 70% to 90% by volume alcohol.

18. A method as claimed in claim 17 wherein the excess amount of the first foaming agent is 1 to 3 times the base amount.

* * * * *